(12) United States Patent
Fukushima et al.

(10) Patent No.: US 9,825,232 B2
(45) Date of Patent: Nov. 21, 2017

(54) ELECTRONIC DEVICE USING ORGANIC THIN FILM, AND ELECTRONIC APPARATUS CONTAINING THE SAME

(71) Applicant: JAPAN SCIENCE AND TECHNOLOGY AGENCY, Kawaguchi-shi, Saitama (JP)

(72) Inventors: Takanori Fukushima, Yokohama (JP); Yoshiaki Shoji, Yokohama (JP); Fumitaka Ishiwari, Yokohama (JP); Tsuyoshi Sekitani, Tokyo (JP); Takao Someya, Tokyo (JP)

(73) Assignee: JAPAN SCIENCE AND TECHNOLOGY AGENCY, Kawaguchi-shi (JP)

(*) Notice: Subject to any disclaimer, the term of this patent is extended or adjusted under 35 U.S.C. 154(b) by 157 days.

(21) Appl. No.: 14/767,032

(22) PCT Filed: Aug. 21, 2013

(86) PCT No.: PCT/JP2013/004954
§ 371 (c)(1),
(2) Date: Aug. 11, 2015

(87) PCT Pub. No.: WO2014/125527
PCT Pub. Date: Aug. 21, 2014

(65) Prior Publication Data
US 2016/0005974 A1 Jan. 7, 2016

(30) Foreign Application Priority Data
Feb. 12, 2013 (JP) ................................ 2013-024097

(51) Int. Cl.
*H01L 51/00* (2006.01)
*C07C 69/712* (2006.01)
(Continued)

(52) U.S. Cl.
CPC .......... *H01L 51/0055* (2013.01); *C07C 43/21* (2013.01); *C07C 43/215* (2013.01);
(Continued)

(58) Field of Classification Search
CPC ............. H01L 51/0545; H01L 51/0036; H01L 51/0541; H01L 51/5012
See application file for complete search history.

(56) References Cited

U.S. PATENT DOCUMENTS

| | | | |
|---|---|---|---|
| 8,502,203 B2 * | 8/2013 | Tano | ............ H01L 51/0005 257/40 |
| 2008/0092807 A1 | 4/2008 | Chabinyc et al. | |
| 2009/0105488 A1 * | 4/2009 | Cheng | ................. C07C 43/21 548/440 |

FOREIGN PATENT DOCUMENTS

| | | |
|---|---|---|
| CN | 1707811 A | 12/2005 |
| CN | 102714276 A | 10/2012 |

(Continued)

OTHER PUBLICATIONS

Liu et al., "Deposition of Metal-Organic Frameworks by Liquid-Phase Epitaxy: The Influence of Substrate Functional Group Density on Film Orientation", Materials, May 2012, pp. 1581-1592, cited in ISR filed in IDS on Aug. 11, 2015 (2 pages).

(Continued)

*Primary Examiner* — Quoc Hoang
(74) *Attorney, Agent, or Firm* — Westerman, Hattori, Daniels & Adrian, LLP

(57) ABSTRACT

The present invention provides a high-performance, highly homogeneous, highly stable electronic device by forming an extremely uniform interface between an insulator and an organic semiconductor, as well as an electronic apparatus using the same. The present invention relates to an electronic device which contains, as a component, an organic thin film in which a geometric two-dimensional arrangement is (Continued)

formed regularly by interdigitating skeletal structures of a positive three-pronged shape of triptycene and by adding a first molecule extending out of one plane of a two-dimensional molecular structure of the triptycene skeletal structure. The invention also relates to an electronic apparatus and the like which contains the electronic device in the interior of the electronic apparatus.

24 Claims, 7 Drawing Sheets

(51) Int. Cl.
    *C07C 43/21* (2006.01)
    *C07C 43/215* (2006.01)
    *H01L 51/05* (2006.01)
    *C07C 43/225* (2006.01)
    *C07C 69/734* (2006.01)
    *H01L 49/02* (2006.01)

(52) U.S. Cl.
    CPC .......... *C07C 43/225* (2013.01); *C07C 69/712* (2013.01); *C07C 69/734* (2013.01); *H01L 28/40* (2013.01); *H01L 51/0558* (2013.01); *C07C 2603/86* (2017.05); *C07C 2603/90* (2017.05); *H01L 51/005* (2013.01)

(56) References Cited

FOREIGN PATENT DOCUMENTS

| | | | |
|---|---|---|---|
| JP | 2002-363154 | A | 12/2002 |
| JP | 2004-33824 | A | 2/2004 |
| JP | 2004-315461 | A | 11/2004 |
| JP | 2007-194360 | A | 8/2007 |
| JP | 2007-277171 | A | 10/2007 |
| JP | 2008-075047 | A | 4/2008 |
| JP | 2009-188259 | A | 8/2009 |
| JP | 2012-111716 | A | 6/2012 |
| JP | 2012-156542 | A | 8/2012 |
| JP | 2012-174805 | A | 9/2012 |
| WO | 03/055853 | A1 | 7/2003 |
| WO | 2012/077625 | A1 | 6/2012 |
| WO | 2014/111980 | A1 | 7/2014 |

OTHER PUBLICATIONS

Nishinaka et al., "Janus-gata Triptycene o Platform to suru Denshi Oyobi Hikari Kassei Kinodan no Ko Mitsudo Shusekika", Dai 23 Kai Symposium on Physical Organic Chemistry Yoshishu, Sep. 5, 2012, p. 216, w/English translation, cited in ISR filed in IDS on Aug. 11, 2015 (3 pages).

Nishinaka et al., "Janus-gata Triptycene o Platform to suru Denshi Oyobi Hikari Kassei Kinodan no Ko Mitsudo Shusekika", Dai 23 Kai Symposium on Physical Organic Chemistry Poster Bunsho, Sep. 19, 2012, cited in ISR filed in IDS on Aug. 11, 2015 (4 pages).

Seiki et al., "Nijigen Bunshi Shusekitai no Kochiku e Muketa Janus-gata Triptycene Yudotai no Design", Dai 23 Kai Symposium on Physical Organic Chemistry Yoshishu, Dai 23 Kai Symposium on Physical Organic Chemistry Jikko linkai Jimukyoku, Sep. 5, 2012, p. 217, w/English translation, cited in ISR filed in IDS on Aug. 11, 2015 (4 pages).

Seiki et al., "Nijigen Bunshi Shusekitai no Kochiku e Muketa Janus-gata Triptycene Yudotai no Design", Dai 23 Kai Symposium on Physical Organic Chemistry Poster Bunsho, Sep. 19, 2012, cited in ISR filed in IDS on Aug. 11, 2015 (4 pages).

Shoji et al., "Janus-gata Triptycene: Kinodan no Seimitsu katsu Ko Mitsudo Shusekika o Kano ni suru Han'yosei Bunshi Platform no Kaihatsu", Dai 23 Kai Symposium on Physical Organic Chemistry Yoshishu, Sep. 5, 2012, pp. 30 to 31, cited in ISR filed in IDS on Aug. 11, 2015 (3 pages).

Shoji et al., "Janus-gata Triptycene: Kinodan no Seimitsu katsu Ko Mitsudo Shusekika o Kano ni suru Han'yosei Bunshi Platform no Kaihatsu", Dai 23 Kai Symposium on Physical Organic Chemistry Koto Happyo Bunsho, Sep. 19, 2012, cited in ISR filed in IDS on Aug. 11, 2015 (6 pages).

Seiki et al., "Nijigen Bunshi Shusekitai Kochiku e Muketa Janus-gata Triptycene Yudotai no Kaihatsu", CSJ: The Chemical Society of Japan Shuki Jigyo, Dai 2 Kai CSJ Kagaku Festa 2012 Program, Koen Yokoshu, Sep. 26, 2012, p. 266, (P6-53), w/English translation, cited in ISR filed in IDS on Aug. 11, 2015 (4 pages).

Shimizu et al., "Nijigen Bunshi Shusekitai no Kochiku e Muketa Janus-gata Triptycene Yudotai no Kaihatsu", CSJ: The Chemical Society of Japan Shuki Jigyo, Dai 2 Kai CSJ Kagaku Festa 2012 Poster Bunsho, Oct. 16, 2012, cited in ISR filed in IDS on Aug. 11, 2015 (4 pages).

Fukushima et al., "Nijigen Shusekikano o Yusuru Bunshi Building Block no Kaihatsu", Fuchi Kenkyusho-kan Alliance 'Jisedai Electronics' Group (GI) Bunkakai, Yamagata University Joint Shinpoji, Aug. 5, 2013, p. 32, w/English trnslation, cited in ISR filed in IDS on Aug. 11, 2015 (4 pages).

Shoji et al., "Nijigen Shusekika ni yoru Centimeter Scale no Tankesshojo Bunshi Usumaku no Keisei", Fuchi Kenkyusho-kan Alliance 'Jisedai Electronics' Group (GI) Bunkakai, Yamagata University Joint Shinpoji, Aug. 5, 2013, p. 78, w/English translation, cited in ISR filed in IDS on Aug. 11, 2015 (4 pages).

Hutchins et al., "Effects of self-assembled monolayer structural order, surface homogeneity and surface energy on pentacene morphology and thin film transistor device performance", Journal of Materials Chemistry C, 2013, 1 (1) , pp. 101-113, cited in ISR filed in IDS on Aug. 11, 2015 (4 pages).

Klauk et al., "Ultralow-power organic complementary circuits", Nature05533, Letters, Feb. 15, 2007, vol. 445, pp. 745-748, cited in the specification filed in IDS on Aug. 11, 2015 (4 pages).

Notification of Transmittal of the International Preliminary Report on Patentability (Form PCT/IB/338) of International Application No. PCT/JP2013/004954 dated Aug. 27, 2015 with Forms PCT/IB/373, PCT/IB/237 and PCT/IB/326. (14 pages).

International Search Report dated Nov. 5, 2013, issued in counterpart application No. PCT/JP2013/004954 (3 pages).

Norvez, S. et al., "Epitaxygens: Mesophases based on the Triptycene Molecular Subunit", Journal of the Chemical Society, Jan. 1990, No. 20, pp. 1398-1399, cited in Extended (supplementary) European Search Report dated Aug. 10, 2016. (2 pages).

Navale, T.S. et al, "Charge Delocalizaton in Self-Assembled Mixed-Valence Aromatic Cation Radicals", Langmuir, Jan. 2012, vol. 28, No. 1, pp. 71-83, cited in Extended (supplementary) European Search Report dated Aug. 10, 2016. (13 pages).

Wolpaw, A.J. et al, "Synthesis of Self-Orienting Triptycene Adsorbates for STM Investigations", Tetrahedron Letters, Oct. 2003, vol. 44, No. 41, pp. 7613-7615, cited in Extended (supplementary) European Search Report dated Aug. 10, 2016. (3 pages).

Extended (supplementary) European Search Report dated Aug. 10, 2016, issued in counterpart Application No. 13875096.3. (5 pages).

Office Action dated Apr. 24, 2017, issued in counterpart Chinese application No. 201380071265.4, with English Translation (23 pages).

Rogers, M.E. et al, "Symmetrically Trisubstituted Triptycenes", J. Org. Chem., 1986, vol. 51, No. 17, pp. 3308-3314.

Office Action dated Jul. 21, 2017, issued in counterpart Japanese Application No. 2014-561596, with English machine translation. (13 pages).

* cited by examiner

[Fig. 1]
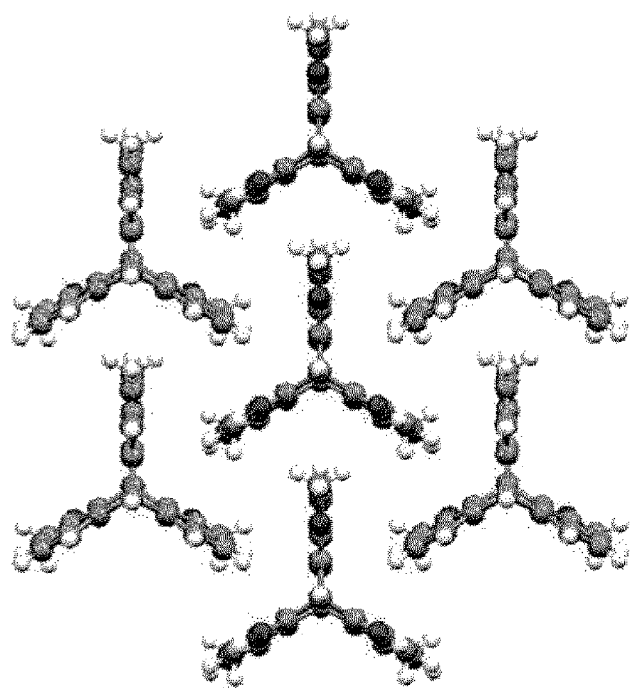
[Fig. 2]
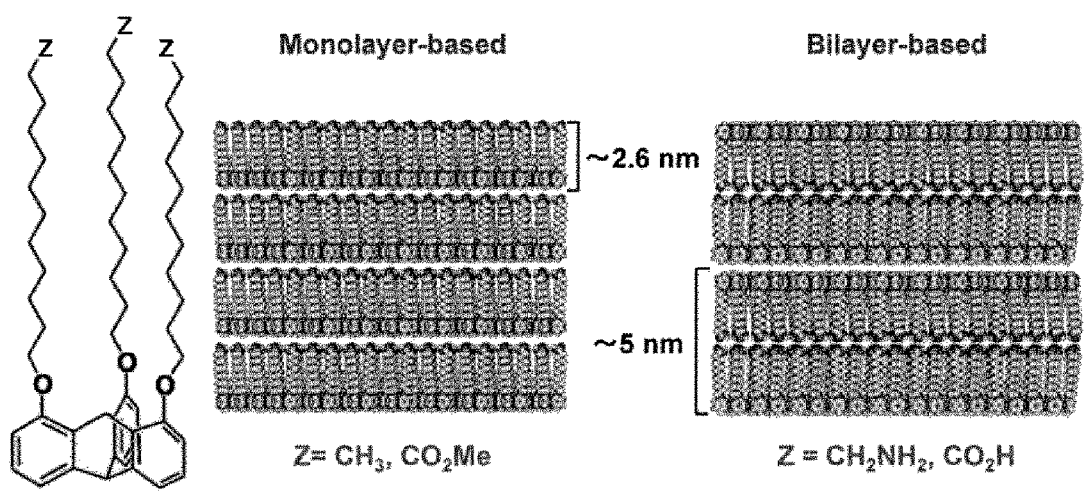

[Fig. 3]
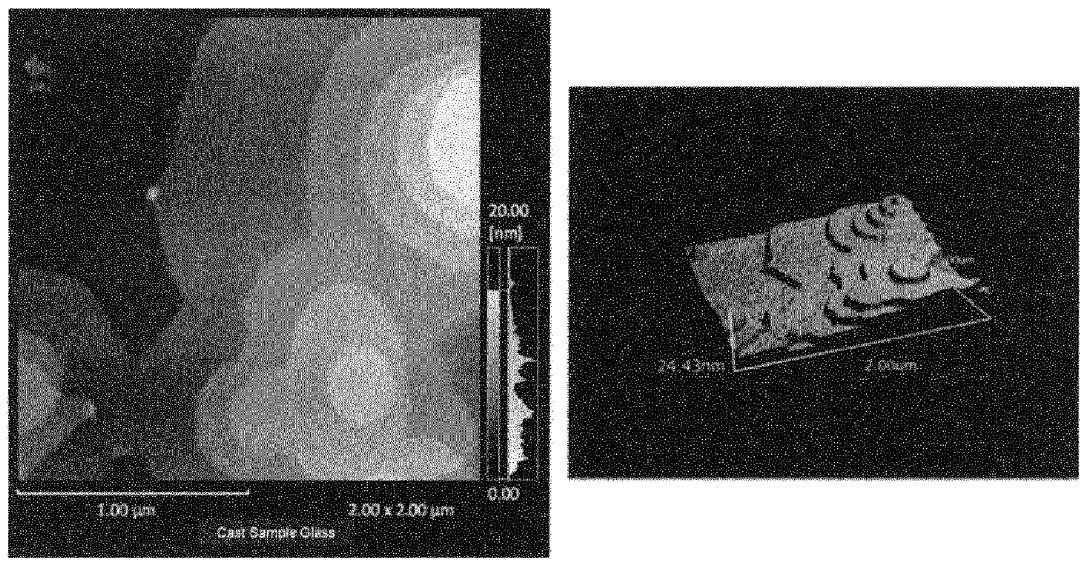
[Fig. 4]
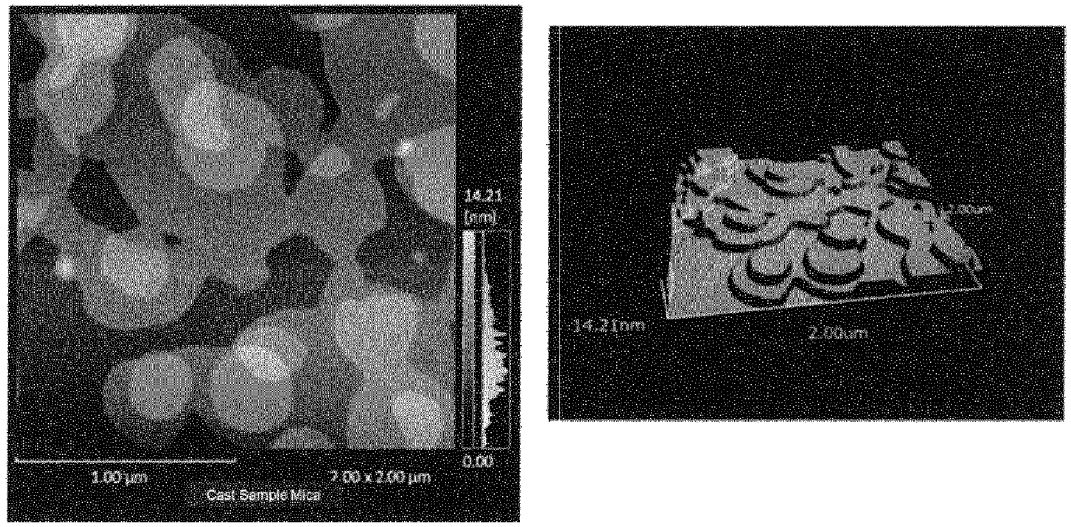

[Fig. 5]
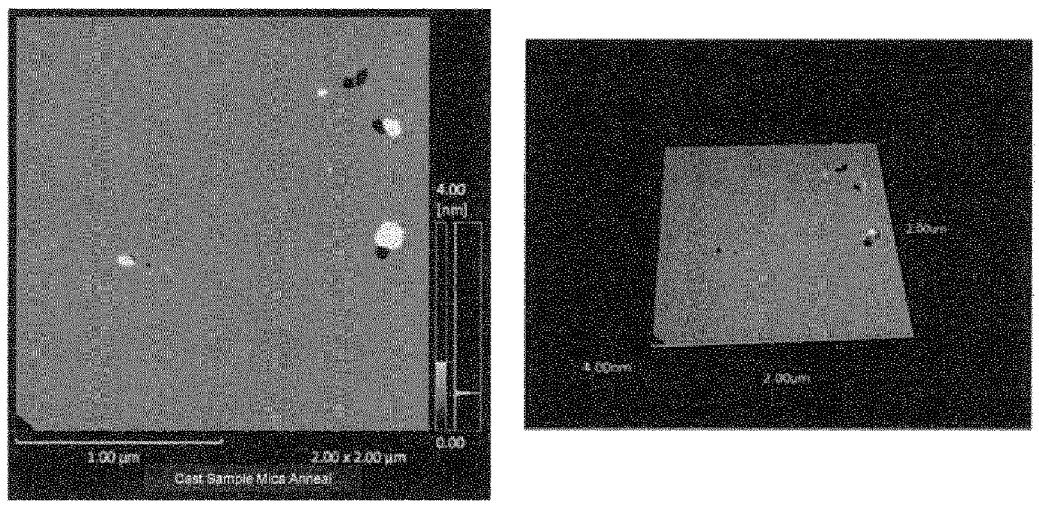
[Fig. 6]
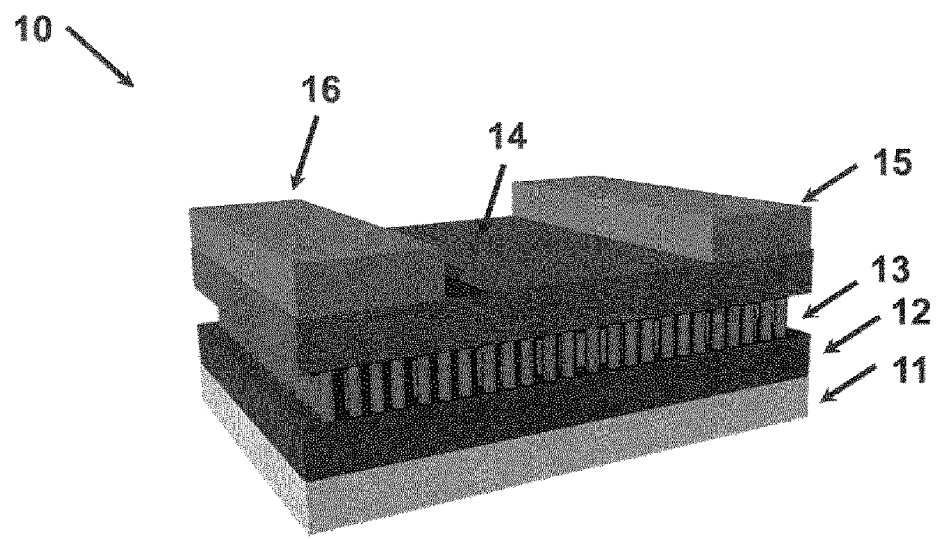

[Fig. 7]
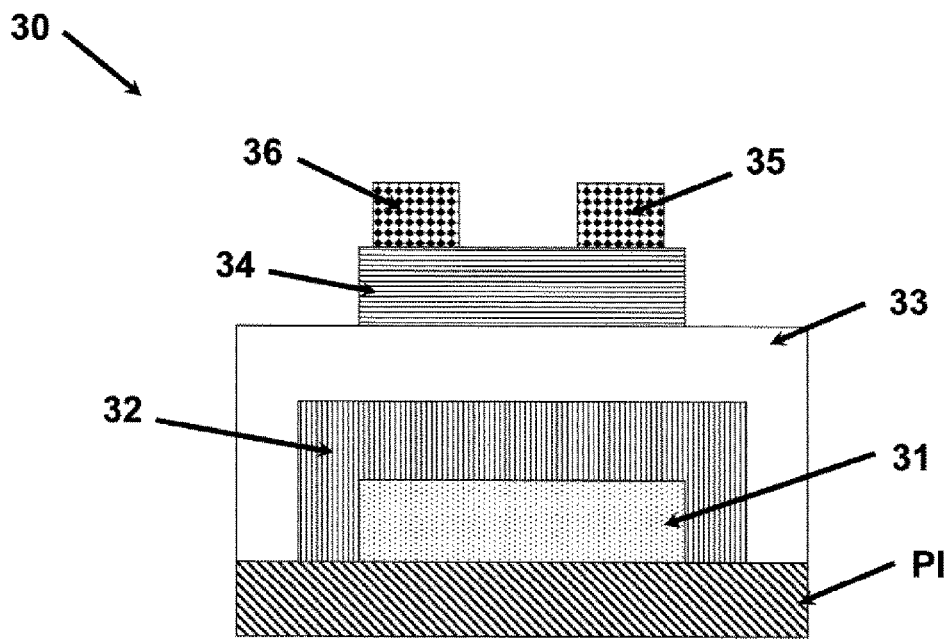
[Fig. 8]
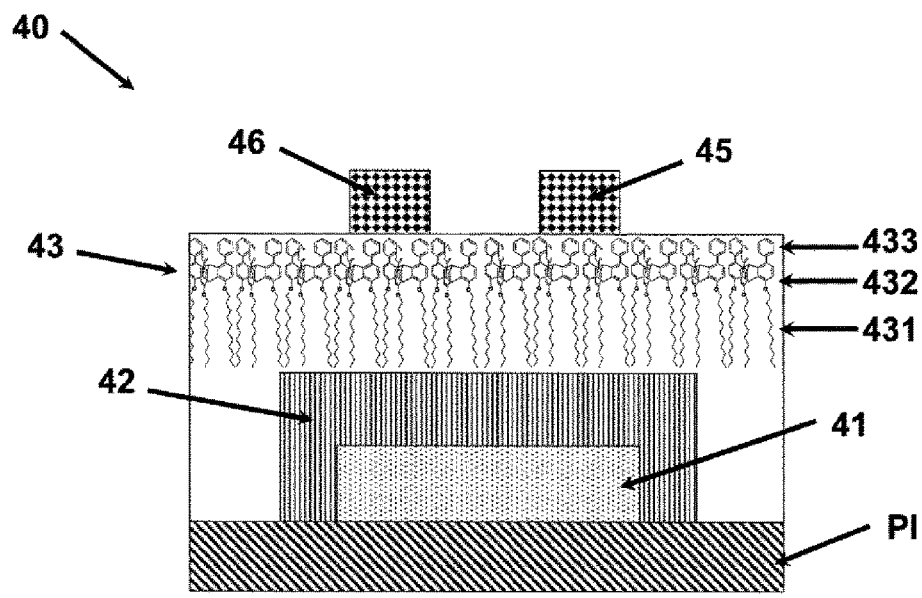

[Fig. 9]
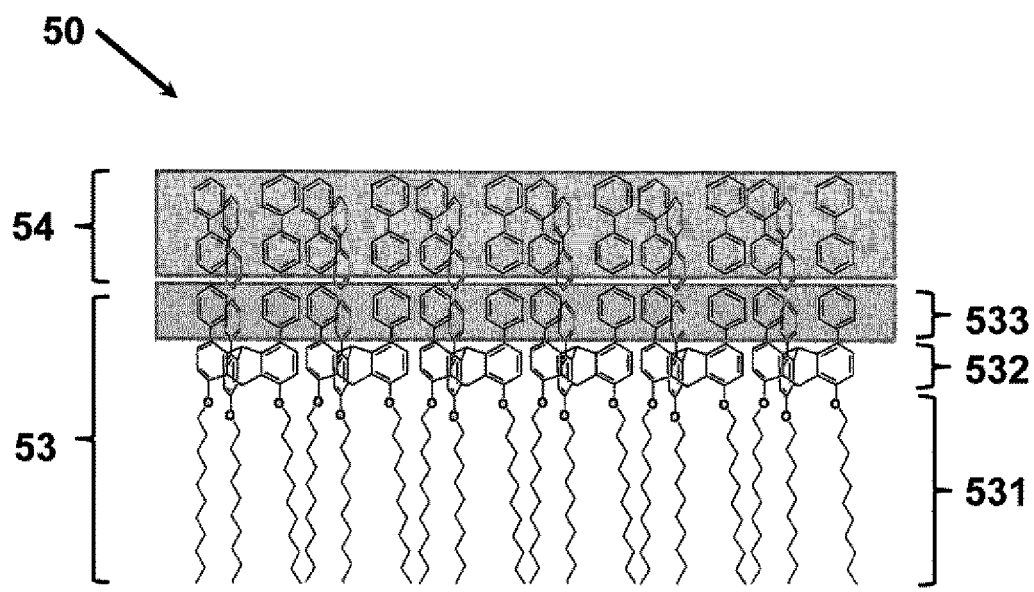
[Fig. 10]
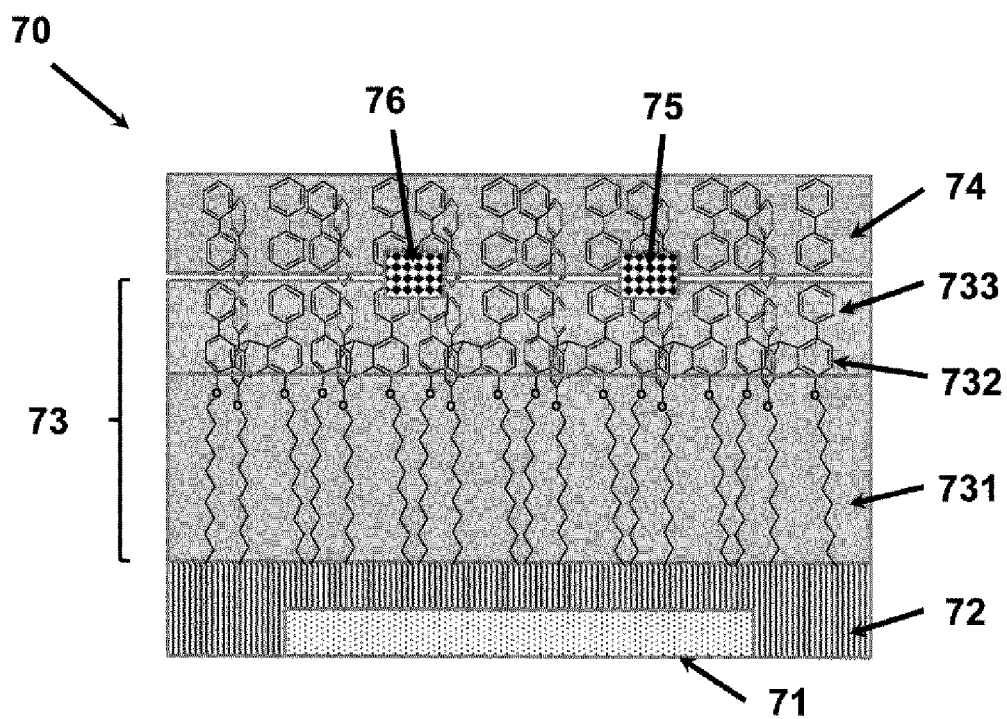

[Fig. 11]
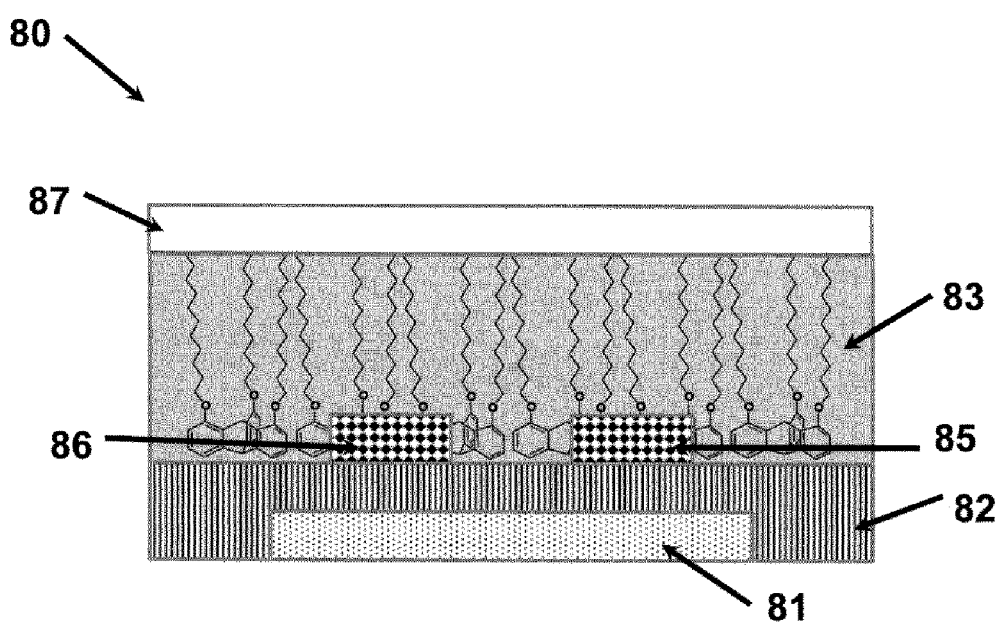

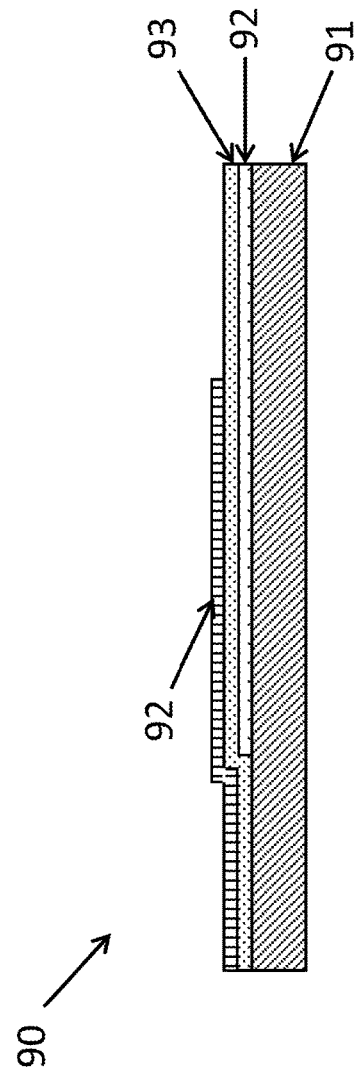
[Fig.12]
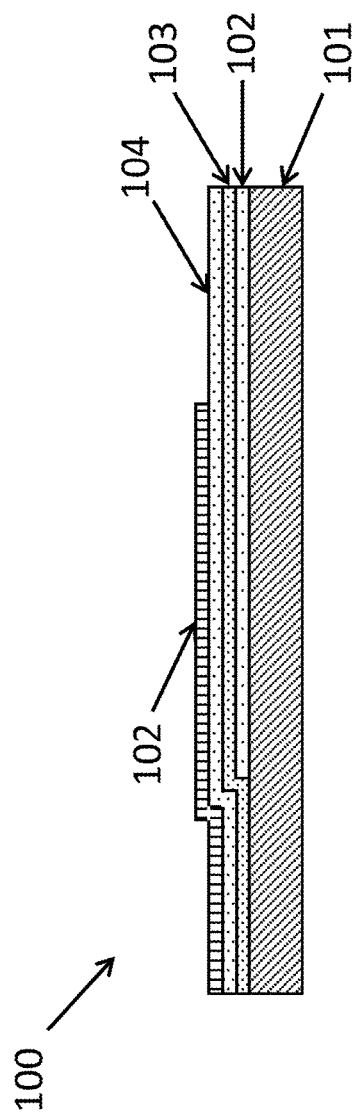
[Fig.13]

ELECTRONIC DEVICE USING ORGANIC THIN FILM, AND ELECTRONIC APPARATUS CONTAINING THE SAME

TECHNICAL FIELD

The present invention relates to an electronic device including, as a component, a film that forms an extremely uniform interface between an insulator and an organic semiconductor, and a circuit board and an electronic apparatus containing the same.

BACKGROUND ART

In a thin film transistor using a semiconductor, a semiconductor thin layer is layered on the surface of an insulator and electrons or holes move through the semiconductor thin layer in the vicinity of this interface between the insulator and the semiconductor. In the case of an organic semiconductor material, the organic semiconductor material is heated to evaporate and attach the material to the surface of an insulator. At this time, the microscopic surface state of the insulator, in detail, surface roughness, substances adsorbed on the surface, surface molecular defect and the like affect the performance of the thin film transistor and significantly deteriorates the performance in many cases. In addition, a coating method is known in which a solution prepared by dissolving an organic semiconductor material in a solvent is coated on the surface of an insulator and the solvent is removed so as to form a thin film composed of the organic semiconductor material. This coating method is for easily spreading out the solution on a large-area substrate and thus to achieve a large-area organic electronic device. However, the solvent used in the coating method changes the nature of the surface of the insulator substrate and deteriorates the interface, and thus the organic thin film transistor fabricated have a decrease in performance such as an increase in driving voltage or an increase in leakage current in some cases.

In order to prevent such a decrease in performance, attempts to homogenize the surface and the interface after layering by subjecting the surface of the insulator substrate to a special surface treatment have been made. More specifically, a method is known in which a self-assembled monolayer (hereinafter, also referred to as SAM) is formed at the interface between the insulator and the organic semiconductor.

However, a SAM having a thiol group (—SH) of the related art can be formed only on a limited surface of a metal such as gold, or the like.

In addition, a SAM material having a phosphoric acid group or a phosphonic acid group has recently been proposed (see Non Patent Literature 1).

This novel SAM material interacts with a wide variety of metal oxide surfaces and is able to form an organized monolayer. However, the formation of the SAM on the surface of organic materials is limited.

As described above, the SAM material of the related art can be formed on a limited surface and is also greatly affected by the surface state. Particularly, in the case of employing a metal oxide as an insulating layer to form an organic semiconductor, a trouble that a SAM is not normally formed due to the unevenness of the surface tends to be caused and there is a problem that inferior quality is unavoidable when a SAM is applied to a large area in particular.

As described above, although the quality management at the interface between the insulator and the organic semiconductor is important in a thin film transistor, an additional treatment complicates the manufacturing method and also there is a problem that the quality management is difficult. Furthermore, there is also a problem that the expected properties are exhibited in the earlier stage after the fabrication but the interface changes along with the drive of the device, and the performance changes and deteriorates with the elapse of use time.

In addition, it is possible to impart a specific function to the surface of a solid substrate by bonding a functional group exhibiting functionality to a moiety of the molecule forming the SAM. For example, it is possible to impart various functions such as electron transfer and oxidation-reduction reactions, catalysis, light-induced electron transfer, electrochemical luminescence, recognition of ions and molecules, bio-sensors, bio-molecular devices, and photovoltaic power generation to the surface of a solid substrate by the formation of a SAM, and the application of a SAM in these fields is expected.

For example, formation of a SAM using, as a material, an alkylenethiol compound having an amino group as an end group for fixing a saccharide having an aldehyde moiety or a compound having a carboxyl group (see Patent Literature 1), formation of a SAM using an alkylenethiol compound having an electron accepting functional group such as a cyano aryl group at an end group, and the like as a material (see Patent Literature 2), formation of a SAM exhibiting ultraviolet resistance using an alkylenethiol compound having a polyphenylene group at an end group, and the like as a material (see Patent Literature 3), formation of a SAM having a rigid adamantane surface film structure using bis(adamantylmethyl)disulfide (see Patent Literature 4), formation of a SAM for lithography that is able to be patterned with light having a long wavelength by the introduction of a functional group sensitive to light having a relatively long wavelength in the middle of an alkylene chain (see Patent Literature 5), formation of a SAM for a photovoltaic cell and a photocharge separating element using a compound obtained by covalently bonding a pyrrole ring-expanded porphyrin and a fullerene (see Patent Literature 6), and the like have been reported.

CITATION LIST

Patent Literature

Patent Literature 1: JP 2002-363154 A
Patent Literature 2: WO 2003-055853 A
Patent Literature 3: JP 2004-33824 A
Patent Literature 4: JP 2004-315461 A
Patent Literature 5: JP 2007-277171 A
Patent Literature 6: JP 2012-111716 A

Non Patent Literature

Non Patent Literature 1: Klauk, et al., Nature, 445, 745 (2007)

SUMMARY OF INVENTION

Technical Problem

The present invention provides a high-performance, highly homogeneous and highly stable electronic device by forming an extremely uniform interface between an insulator and an organic semiconductor. The electronic device of the present invention has an extremely uniform interface between an insulator and an organic semiconductor, thus an electronic device exhibiting a low noise level is realized, and as a result, the electronic device is able to detect a weak signal, for example, a signal emanating from a living body with high sensitivity. Furthermore, the film to form the interface of the present invention can be flexible and applied to a large area, and consequently a flexible large-area electronic device is provided.

Solution to Problem

The present inventors have studied to regiospecifically and face-specifically introduce a plurality of groups having functions to triptycene. Moreover, the present inventors have found out that in a triptycene derivative which face-specifically has three identical substituents on one side of triptycene, benzene rings arranged in a three-blade shape of triptycene (skeletal structure of triptycene having a positive three-pronged shape) are integrated in a nesting shape (see FIG. 1), and in a case in which the three identical substituents have a relatively long carbon chain, these substituents are arranged and integrated in the same direction to form a film. It has been also found out that the film formed to have such a configuration is self-assembled and this can be converted into a self-assembled monolayer by being further treated.

Furthermore, the present inventors have found out that it is possible not only to form a high-quality film that is extremely uniform and excellent in stability regardless of the nature of material, the surface state and the like of the insulating layer but also to impart a layer having a function of an organic semiconductor or the like at the same time by forming this on the insulating layer of an electronic device.

In other words, the present invention relates to an electronic device including, as a component, an organic thin film having a regular and geometrical two-dimensional molecular arrangement formed by interdigitating the skeletal structures of triptycene having a positive three-pronged shape with one another and adding a first molecule extending out of one plane of the two-dimensional molecular arrangement to the triptycene skeletal structure.

In addition, the present invention relates to an electronic device including, as a component, an organic thin film having insulating properties by the first molecule on one plane of the two-dimensional molecular arrangement of the triptycene skeletal structure and semiconductor properties on the other plane thereof by further adding the second molecule with a function of a semiconductor to the other plane of the two-dimensional molecular arrangement of the triptycene skeletal structure.

In more detail, the present invention relates to an electronic device including, as a component, an organic thin film containing a Janus-type triptycene derivative represented by the following Formula [I];

[Chemical Formula 1]

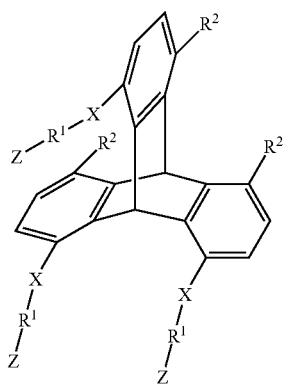

[I]

(in Formula [I], three $R^1$'s are an identical group, $R^1$ represents a divalent saturated or unsaturated hydrocarbon group having from 2 to 60 carbon atoms, the hydrocarbon group may optionally have one or more substituents, and one or more carbon atoms in the hydrocarbon group may be optionally substituted with oxygen atom, sulfur atom, silicon atom, or —$NR^5$— (here, $R^5$ represents a hydrogen atom, an alkyl group having from 1 to 10 carbon atoms, or an aryl group having from 6 to 30 carbon atoms), three $R^2$'s are the same as or different from one another and each independently represent a group different from a group —X—$R^1$—Z, and $R^2$ represents a hydrogen atom, a halogen atom, a hydroxyl group, a nitro group, a cyano group, an amino group, a mono alkyl-substituted amino group, a dialkyl-substituted amino group, an alkyl group which has from 1 to 10 carbon atoms and may optionally have one or more substituents, an alkenyl group which has from 2 to 10 carbon atoms and may optionally have one or more substituents, an alkynyl group which has from 2 to 10 carbon atoms and may optionally have one or more substituents, an alkoxy group which has from 1 to 10 carbon atoms and may optionally have one or more substituents, an alkylthio group which has from 1 to 10 carbon atoms and may optionally have one or more substituents, a formyl group, an alkylcarbonyl group which has from 1 to 10 carbon atoms and may optionally have one or more substituents, an alkoxycarbonyl group which has from 1 to 10 carbon atoms and may optionally have one or more substituents, an alkylcarbonyloxy group which has from 1 to 10 carbon atoms and may optionally have one or more substituents, an aryl group which has from 6 to 30 carbon atoms and may optionally have one or more substituents, or a 5- to 8-membered heteroaryl group which has from 1 to 5 heteroatoms selected from the group consisting of nitrogen atom, oxygen atom, and sulfur atom and from 2 to 10 carbon atoms and may optionally have one or more substituents, three X's are an identical group, and X represents a linker group consisting of a divalent atomic group composed of from 1 to 5 atoms selected from the group consisting of nitrogen atom, oxygen atom, sulfur atom, carbon atom, and silicon atom, and one or more hydrogen atoms if necessary, and three Z's are an identical group, and Z represents a hydrogen atom, a group capable of being bonded to or adsorbed on a surface of a solid substrate, or an end group consisting of a monovalent atomic group composed of from 1 to 15 atoms selected from the group consisting of nitrogen atom, oxygen atom, sulfur atom, carbon atom, phosphorus atom, halogen atom, and silicon atom, and one or more hydrogen atoms if necessary).

In addition, the present invention relates to use of the Janus-type triptycene derivative represented by Formula [I] in an organic thin film as a component of an electronic device.

Moreover, the present invention relates to a circuit board including an electronic device in an electronic circuit, the electronic device including an organic thin film containing the Janus-type triptycene derivative represented by Formula [I] as a component.

Furthermore, the present invention relates to an electronic apparatus including an electronic device in the interior of the electronic apparatus, the electronic device including an organic thin film containing the Janus-type triptycene derivative represented by Formula [I] as a component.

In addition, the present invention relates to an organic thin film forming composition containing the Janus-type triptycene derivative represented by Formula [I] and an organic thin film forming carrier.

Furthermore, the present invention relates to an electronic device material including an organic thin film containing the Janus-type triptycene derivative represented by Formula [I].

More detailed description on the aspect of the present invention is as follows.

(1) An electronic device including, as a component, an organic thin film in which a geometric two-dimensional molecular arrangement of the triptycene skeletal structure is formed regularly by interdigitating skeletal structures of a positive three-pronged shape of triptycene and by adding a first molecule extending out of a plane of a two-dimensional molecular arrangement of the triptycene skeletal structure.

(2) The electronic device according to (1), in which triptycene to which the first molecule is added is the Janus-type triptycene derivative represented by Formula [I].

(3) The electronic device according to (1) or (2), the electronic device including, as a component, an organic thin film having insulating properties by the first molecule on one plane of the two-dimensional molecular arrangement of the triptycene skeletal structure and semiconductor properties on the other plane thereof by further adding the second molecule with a function of a semiconductor to the other plane of the two-dimensional molecular arrangement of the triptycene skeletal structure.

(4) The electronic device according to (3), in which triptycene to which the first molecule and the second molecule are added is the Janus-type triptycene derivative represented by Formula [I].

(5) The electronic device according to (4), in which $R^2$ in the Janus-type triptycene derivative represented by Formula [I] is a group having a function of an organic semiconductor.

(6) An electronic device including an organic thin film containing the Janus-type triptycene derivative represented by Formula [I] as a component.

(7) The electronic device according to (6), in which three $R^2$'s in the Janus-type triptycene derivative represented by Formula [I] are all an identical group.

(8) The electronic device according to (6), in which three $R^2$'s in the Janus-type triptycene derivative represented by Formula [I] are groups different from one another.

(9) The electronic device according to any one of (6) to (8), in which X in the Janus-type triptycene derivative represented by Formula [I] is a divalent group represented by —$CH_2$—, —CH=CH—, —O—, or —$NR^6$— (here, $R^6$ represents a hydrogen atom or an alkyl group having from 1 to 4 carbon atoms).

(10) The electronic device according to (9), in which X in the Janus-type triptycene derivative represented by Formula [I] is a divalent group represented by —$CH_2$—, —CH=CH—, or —O—.

(11) The electronic device according to any one of (6) to (10), in which $R^1$ in the Janus-type triptycene derivative represented by Formula [I] is an alkylene group having from 2 to 30 carbon atoms, an alkenylene group having from 2 to 30 carbon atoms, an alkynylene group having from 2 to 30 carbon atoms, or a divalent arylene group having from 6 to 60 carbon atoms which contains an aryl ring having from 6 to 30 carbon atoms.

(12) The electronic device according to (11), in which $R^1$ in the Janus-type triptycene derivative represented by Formula [I] is an alkylene group having from 2 to 30 carbon atoms, and a divalent arylene group having from 6 to 60 carbon atoms which contains an aryl ring having from 6 to 30 carbon atoms.

(13) The electronic device according to any one of (6) to (12), in which Z in the Janus-type triptycene derivative represented by Formula [I] is a hydrogen atom, a haloalkyl group having from 1 to 10 carbon atoms, an alkenyl group having from 2 to 10 carbon atoms, an alkynyl group having from 2 to 10 carbon atoms, a hydroxyl group, —$COOR^7$ (here, $R^7$ represents a hydrogen atom or an alkyl group which has from 1 to 5 carbon atoms and may optionally have one or more substituents), —$N(R^8)_2$ (here, $R^8$'s may be the same as or different from each other and represent a hydrogen atom, an alkyl group which has from 1 to 5 carbon atoms and may optionally have one or more substituents, or an aryl group which has from 6 to 30 carbon atoms and may optionally have one or more substituents), or —P(=O)($OR^{15}$)$_2$ (here, $R^{15}$'s each independently represent a hydrogen atom, an alkyl group having from 1 to 10 carbon atoms, or an aryl group having from 6 to 12 carbon atoms).

(14) The electronic device according to (13), in which Z in the Janus-type triptycene derivative represented by Formula [I] is a hydrogen atom, —$CF_3$, —CH=$CH_2$, —C≡CH, —$COOR^7$ (here, $R^7$ represents a hydrogen atom or an alkyl group which has from 1 to 5 carbon atoms and may optionally have one or more substituents), —$NH_2$, or —$N(Ar^1)_2$ (here, $Ar^1$'s may be the same as or different from each other and each independently represent an aryl group which has from 6 to 30 carbon atoms and may optionally have one or more substituents).

(15) The electronic device according to any one of (6) to (14), in which $R^2$ in the Janus-type triptycene derivative represented by Formula [I] is a hydrogen atom, a halogen atom, a hydroxyl group, a nitro group, an alkoxy group which has from 1 to 10 carbon atoms and may optionally have one or more substituents, or an aryl group which has from 6 to 30 carbon atoms and may optionally have one or more substituents.

(16) The electronic device according to (15), in which $R^2$ in the Janus-type triptycene derivative represented by Formula [I] is a hydrogen atom, a halogen atom, or an alkoxy group which has from 1 to 10 carbon atoms and may optionally have one or more substituents.

(17) The electronic device according to any one of (6) to (14), in which $R^2$ in the Janus-type triptycene derivative represented by Formula [I] is a group having a function of an organic semiconductor.

(18) The electronic device according to (17), in which $R^2$ in the Janus-type triptycene derivative represented by Formula [I] is an aryl group which has from 6 to 30 carbon atoms and may optionally have one or more substituents or a 5- to 8-membered heteroaryl group which has from 1 to 5 heteroatoms selected from the group consisting of nitrogen atom, oxygen atom, and sulfur atom and from 2 to 10 carbon atoms and may optionally have one or more substituents.

(19) The electronic device according to any one of (1) to (18), in which the organic thin film is a SAM.

(20) The electronic device according to any one of (1) to (19), in which the electronic device is a transistor, a capacitor, a diode, a thyristor, an electroluminescent device, a sensor, or a memory.

(21) The electronic device according to (20), in which the electronic device is a transistor.

(22) The electronic device according to (20) or (21), in which the transistor is a thin film transistor.

(23) The electronic device according to (22), in which the thin film transistor is an organic thin film transistor including a gate electrode, a source electrode, a drain electrode, and a gate insulating layer on a substrate.

(24) The electronic device according to (23), in which the gate insulating layer includes an insulating material and an organic thin film containing the Janus-type triptycene derivative represented by Formula [I].

(25) The electronic device according to (24), in which the gate insulating layer includes a layered body of the insulating material and the organic thin film.

(26) The electronic device according to (24) or (25), in which the insulating material of the gate insulating layer is an organic insulating material.

(27) The electronic device according to (26), in which the organic insulating material is a polyimide, poly(methyl methacrylate) and/or Parylene (registered trademark).

(28) The electronic device according to any one of (24) to (27), in which the organic thin film containing the Janus-type triptycene derivative represented by Formula [I] is an organic thin film that contains a group having a function of an organic semiconductor.

(29) The electronic device according to any one of (22) to (28), in which the thin film transistor further includes a channel layer formed of a semiconductor.

(30) The electronic device according to (29), in which the semiconductor is an organic semiconductor.

(31) The electronic device according to (29) or (30), in which the channel layer is an organic semiconductor layer.

(32) The electronic device according to any one of (29) to (31), in which the organic thin film and the semiconductor of the channel layer are layered.

(33) The electronic device according to any one of (29) to (32), in which a boundary portion between the gate insulating layer and the organic semiconductor layer in the thin film transistor includes the organic thin film according to any one of (1) to (19).

(34) The electronic device according to (33), in which the gate insulating layer, the organic thin film and the organic semiconductor layer are in a layered structure.

(35) The electronic device according to (33) or (34), in which an —X—$R^1$—Z (first molecule) side of the triptycene derivative represented by Formula [I] of the organic thin film is oriented on the insulator layer side and an $R^2$ (second molecule) side of the triptycene derivative represented by Formula [I] of the organic thin film is oriented on the organic semiconductor layer side.

(36) The electronic device according to any one of (29) to (35), in which the source electrode and/or the drain electrode of the thin film transistor is formed between the organic thin film and the channel layer.

(37) The electronic device according to (36), in which the channel layer is an organic semiconductor layer.

(38) The electronic device according to (20), in which the electronic device is a capacitor.

(39) The electronic device according to (38), in which the capacitor is a capacitor having a dielectric layer composed of the organic thin film according to any one of (1) to (19) between electrodes.

(40) The electronic device according to (39), in which the dielectric layer further contains a second dielectric.

(41) The electronic device according to (40), in which the second dielectric is an organic dielectric.

(42) The electronic device according to (40) or (41), in which the organic thin film and the second dielectric are in a layered structure.

(43) Use of the Janus-type triptycene derivative represented by Formula [I] in an organic thin film as a component of an electronic device.

(44) The use according to (43), in which the organic thin film is a SAM.

(45) The use according to (43) or (44), in which the electronic device is the electronic device according to any one of (1) to (42).

(46) A circuit board including the electronic device according to any one of (1) to (42) in an electronic circuit.

(47) The circuit board according to (46), being a thin film circuit board.

(48) The circuit board according to (46) or (47), being a circuit board provided with a thin film circuit board provided with a thin film transistor.

(49) The circuit board according to any one of (46) to (48), being a pixel driving circuit of a display device (so-called flat panel display) such as a liquid crystal display device or an organic EL display device.

(50) An electronic apparatus including the electronic device according to any one of (1) to (42) in the interior thereof.

(51) The electronic apparatus according to (50), being an electronic paper, an organic EL display, or a liquid crystal display.

(52) The electronic apparatus according to (50) or (51), the electronic apparatus being a medical electronic apparatus such as a cardiac potential measuring device, a muscle potential measuring device or a brain potential measuring device.

(53) The electronic apparatus according to (50) or (51), the electronic apparatus being a television, a view finder type or monitor direct view type video tape recorder, a car navigation system, a pager, an electronic notebook, an electronic calculator, an electronic newspaper, a word processor, a personal computer, a workstation, a videophone, a POS terminal, an apparatus provided with a touch panel, or the like.

(54) An organic thin film forming composition including the Janus-type triptycene derivative represented by Formula [I] and an organic thin film forming carrier.

(55) The organic thin film forming composition according to (54), in which the organic thin film is a SAM.

(56) The organic thin film forming composition according to (54) or (55), in which the organic thin film forming carrier is an organic solvent.

(57) The organic thin film forming composition according to (56), in which the organic solvent is dimethylformamide (DMF) or tetrahydrofuran (THF).

(58) An electronic device material including an organic thin film containing the Janus-type triptycene derivative represented by Formula [I].

(59) The electronic device material according to (58), in which the organic thin film is a SAM.

(60) A method of manufacturing the electronic device according to any one of (6) to (42), in which an organic thin film containing the Janus-type triptycene derivative represented by Formula [I] is provided in an electronic device.

(61) The manufacturing method according to (60), in which the method of providing an organic thin film is a method of coating and drying an organic thin film forming composition containing the Janus-type triptycene derivative represented by Formula [I] and an organic thin film forming carrier.

(62) The manufacturing method according to (61), which further includes a process of annealing.

(63) The manufacturing method according to (60), in which the method of providing an organic thin film is a method of installing an organic thin film produced at a liquid-liquid interface in an electronic device.

Advantageous Effects of Invention

The use of the organic thin film of the present invention makes it possible to form an extremely uniform and clean interface between an organic semiconductor layer and an insulator layer, and thus it is possible to achieve an improvement in performance, homogeneity, and stability of an electronic device, in particular, an organic thin film transistor. Furthermore, it is possible to form a uniform electronic device, in particular, a transistor over a large area upon realizing a large-area flexible electronic device.

In addition, in another aspect of the present invention, a molecular moiety which functions as a semiconductor and a molecular moiety which functions as an insulator are incorporated in one molecule, and the molecule forms a monolayer. One side of the monolayer can exhibit semiconductor properties, and the other side can form a layered structure of insulator layers. This makes it possible to form an extremely homogeneous boundary between a semiconductor and an insulator and thus to realize a transistor without disturbance at the interface. It is possible to homogeneously and stably fabricate a semiconductor element having the performance of high mobility, high durability and a low leakage current which cannot be obtained by the technique of the related art as the disturbance at the interface ultimately disappears.

Moreover, the structure of the monolayer of the present invention is defined by the geometric shape of the triptycene skeletal structure, and thus the resulting monolayer is not affected by the surface state of the lower layer or the upper layer. This makes it possible to realize a high-performance electronic device combined with various substrates.

The electronic device of the present invention can realize an extremely high-performance flexible organic semiconductor device, and large-area flexible organic electronics can be applied to various kinds of displays, electronic paper or the like and can be employed not only to a personal computer, a portable terminal and home appliances but also to a medical field.

BRIEF DESCRIPTION OF DRAWINGS

FIG. 1 is a view schematically illustrating a state in which benzene rings arranged in a three-blade shape of triptycene (skeletal structure of triptycene having a positive three-pronged shape) are integrated in a nesting shape when the triptycene skeletal structure in an organic thin film of the present invention is viewed from a direction transverse to the three benzene rings of the triptycene skeletal structure.

FIG. 2 is a view schematically illustrating a state in which a Janus-type triptycene derivative of the present invention is integrated. The example illustrated in FIG. 2 is a case in which $R^1$ is an alkylene group and Z is an ester.

FIG. 3 is a view illustrating the result of AFM measurement for a film produced on a glass substrate using Compound 1 of the present invention.

FIG. 4 is a view illustrating the result of AFM measurement for a film produced on a mica substrate using Compound 1 of the present invention.

FIG. 5 is a view illustrating the result of AFM measurement for a film produced on the mica substrate using Compound 1 of the present invention.

FIG. 6 is a view schematically illustrating a transistor 10 of the present invention.

FIG. 7 is a view illustrating a sectional structure of a transistor 30 of the present invention. The transistor 30 of the present invention is constituted by a gate electrode 31, a gate insulating layer 32, an organic thin film 33 of the present invention, an organic semiconductor layer 34, a drain electrode 35 and a source electrode 36.

FIG. 8 is a view illustrating a transistor 40 of the present invention. The transistor 40 of the present invention is constituted by a gate electrode 41, a gate insulating layer 42, an organic thin film 43 of the present invention, a drain electrode 45 and a source electrode 46.

FIG. 9 is a view illustrating an organic thin film 53 and an organic semiconductor layer 54 of a transistor 50 of the present invention. The organic thin film 53 is composed of an alkyl chain moiety 531, a triptycene skeletal structure moiety 532 and a phenyl group moiety 533.

FIG. 10 is a view illustrating a transistor 70 of the present invention. The transistor 70 of the present invention is constituted by a gate electrode 71, a gate insulating layer 72, an organic thin film 73 of the present invention having a function of an organic semiconductor, an organic semiconductor layer 74, a drain electrode 75 and a source electrode 76.

FIG. 11 is a view illustrating a transistor 80 of the present invention. The transistor 80 of the present invention is constituted by a gate electrode 81, a gate insulating layer 82, an organic thin film 83 of the present invention having a function of an organic semiconductor, a drain electrode 85, a source electrode 86 and a sealing layer 87.

FIG. 12 is a view illustrating capacitor 90 of the present invention formed on substrate 91. The capacitor 90 of the present invention comprises electrodes 92 and first dielectric 93 composed of an organic thin film of the present invention. The dielectric 93 is sandwiched between electrodes 92.

FIG. 13 is a view illustrating capacitor 100 of the present inveniton formed on substrate 101. The capacitor 100 of the present invention comprises electrodes 102, first dielectric 103 composed of an organic thin film of the present invention, and second dielectric 104. The first dielectric 103 and the second dielectric 104 are sandwiched between electrodes 102.

DESCRIPTION OF EMBODIMENTS

Aspects of the present invention will be described in more detail.

"Triptycene" itself is a known compound and is a compound having benzene rings that are arranged in a unique three-blade shape. In the present invention, the position numbers in triptycene are as follows in conformity with the nomenclature by the CAS.

[Chemical Formula 2]

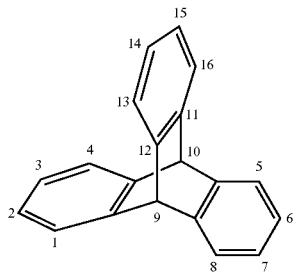

The "Janus-type triptycene derivative" in the present invention refers to a triptycene derivative in which triptycene has two different planes of a plane on positions of 1, 8, and 13 and a plane on positions of 4, 5, and 16, the planes having properties different from each other. Janus is the name of a god who appears in Roman mythology and has different faces in front and the back of the head. The triptycene derivative of the present invention is named "Janus-type" based on the name of the god in Roman mythology since triptycene has two different planes of the plane on positions 1, 8, and 13 and the plane on positions of 4, 5, and 16.

Hence, it can be said that the Janus-type triptycene derivative of the present invention is a triptycene derivative having different properties on two planes of triptycene. The Janus-type triptycene derivative of the present invention is characterized by having two planes of a plane that is involved in the formation of an organic thin film and a plane that is not involved in the formation of the film. In more detail, the Janus-type triptycene derivative of the present invention is a triptycene derivative characterized by having the same substituents for forming an organic thin film only on either plane, for example, only on the plane on positions of 1, 8, and 13. As an even more preferred aspect, an aspect is mentioned in which the three substituents of $R^2$ in Formula [I] of the Janus-type triptycene derivative of the present invention are the same substituents and function as a plane having common properties, but the substituents on this plane are not required to be necessarily the same.

The Janus-type triptycene derivative of the present invention in a case in which X is —O—, $R^1$ is a $C_{11}$ alkylene group, Z is a —COOMe group, and $R^2$ are all a hydrogen atom in Formula [I] of the present invention (hereinafter, referred to as Compound 1) is presented below.

[Chemical Formula 3]

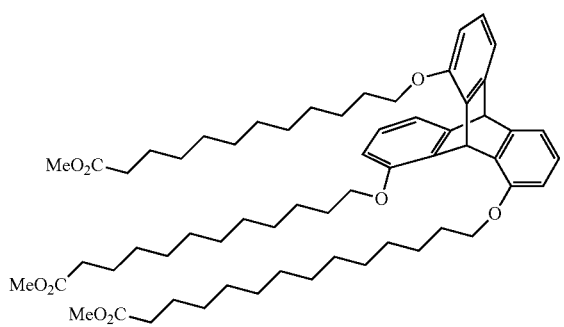

The "benzene rings arranged in a three-blade shape of the triptycene skeletal structure are integrated in a nesting shape" in the present invention refers to a state in which each of the three benzene rings of the triptycene skeletal structure forms a face angle of 120° and the benzene rings of adjacent triptycene enters between the respective benzene rings in a nesting shape, and FIG. 1 schematically illustrates such a state when viewed from the top.

It is a state in which the benzene rings of adjacent triptycene skeletal structure enter between the respective benzene rings arranged in a three-blade shape of a triptycene skeletal structure and this is regularly integrated. The distance from the bridgehead of triptycene to the bridgehead of adjacent triptycene was about 0.81 nm in a case in which Compound 1 exemplified above is integrated.

The "three identical substituents bonded in the same direction of the benzene rings of the triptycene skeletal structure are arranged and integrated in the same direction" in the present invention refers to a state in which three substituents of —X—$R^1$—Z present on one plane of the Janus-type triptycene derivative represented by Formula [I] of the present invention extend in the same direction of the integrated body of the triptycene skeletal structure having the benzene rings integrated in a nesting shape and these are arranged and integrated.

The case in which Z is $CO_2Me$ in FIG. 2 illustrates the state in which Compound 1 exemplified above is integrated. The triptycene layer on the lower side indicates the integrated body of the triptycene skeletal structure in which the benzene rings are integrated in a nesting shape. Moreover, three identical substituents in the same direction of the triptycene layer, on the upper side in the case of FIG. 2 are arranged and integrated in the same direction to form an alkyl layer and an ester layer. The thickness of the layer was about 2.6 nm.

In a case in which three identical substituents are randomly arranged in different directions when the triptycene skeletal structure is integrated, a film in perfect order as illustrated in FIG. 2 is not formed but a lump is formed. However, the present inventors have found out for the first time that these substituents are not randomly arranged but integrated in perfect order in the same direction to form a stable film in a case in which the Janus-type triptycene derivative of the present invention is integrated and have succeeded in forming a regular and stable film in a nano unit.

In addition, as illustrated in FIG. 2, there is also a case in which not a single-layer structure but a two-layer structure in which Z's face each other is formed when the substituent Z is —$CH_2NH_2$ and —COOH. The thickness of the layer in the case of a two-layer structure was about 5 nm.

The "organic thin film" in the present invention refers to an organic thin film formed by integrating the Janus-type triptycene derivative of the present invention in the state described above. The film formed by integrating in this manner is a monolayer in the case of a single-layer and can be said to be a SAM. The film thickness can be adjusted by the number of carbon atoms in the alkylene chain and can be determined in accordance with a general rule of being about 0.2 nm per one carbon atom.

In addition, it is also possible to form a multilayer film by overlapping such a layer. In this case, there is a case in which the layers are overlapped in the same direction and there is a case in which the layers are overlapped to face opposite directions. The state of overlapping is determined depending on the kinds of the Z group and/or the $R^2$ group in Formula [I] or the conditions for film formation.

The film formed by coating a solution (1 mg/200 mL, about 5.3 µM) prepared by dissolving Compound 1 exemplified above in tetrahydrofuran (THF) on a glass substrate and drying it can have a single-layer structure, a two-layer structure, or a three-layer structure. The film thickness in the case of a single-layer structure was about 2.46 nm. The film thickness in the case of a two-layer structure was about 5.4 nm. The film thickness in the case of a three-layer structure was about 7.84 nm. In addition, the film formed by coating the same solution on a mica substrate and drying it can have a single-layer structure or a two-layer structure, and the film thickness in the case of a single-layer structure was about 3.27 nm and the film thickness in the case of a two-layer structure was about 6.45 nm. Furthermore, the film formed by coating the same solution on a mica substrate, drying it, and then annealing it at 180° C. has a single-layer structure, and the film thickness thereof was about 2.04 nm.

The "functional film" in the present invention refers to a film, in particular, an organic thin film obtained by bonding functional groups having various kinds of functions to the film of the present invention described above. In general, a film such as a SAM, is divided into three moieties of a moiety for being bonded to or adsorbed on the surface of a solid substrate, a moiety for obtaining the van der Waals force between alkyl chains such as an alkyl chain to form a stable film, and the end moiety of the molecule. Moreover, it has been known that it is possible to impart various kinds of functions to the organic thin film to be formed by introducing a functional group having an electrochemical function, an optical function, a biological function and the like into the end moiety of the molecule. It is possible to impart various kinds of functions to the organic thin film of the present invention as well by using the end moiety of the molecule in the same manner as the organic thin film of the related art as described above.

As has been described above, the Janus-type triptycene derivative of the present invention has two planes of the "plane of the group —X—$R^1$—Z in Formula [I]" and the "plane of $R^2$ in Formula [I]", and it is possible to introduce functional groups having various functions into the plane of $R^2$ in the same manner as in the film of the related art. In addition, it is essential to have a moiety for being bonded to or adsorbed on the surface of a solid substrate in the film of the related art, but the moiety for being bonded to or adsorbed on a solid surface is not necessarily required in an organic thin film using the Janus-type triptycene derivative of the present invention since not only the van der Waals force is exhibited between the alkyl chains such as an alkyl chain but also the triptycene skeletal structure moiety has film forming ability. Hence, it is also possible to introduce functional groups having various functions into the moiety of the group Z of the Janus-type triptycene derivative represented by Formula [I] of the present invention.

Consequently, a film formed by introducing functional groups having various kinds of functions into the plane that is not involved in the formation of the organic thin film of the Janus-type triptycene derivative of the present invention and/or into the moieties of the group Z of the Janus-type triptycene derivative represented by Formula [I] of the present invention is referred to as the "functional film" in the present invention.

Among such "functional films", as the "functional film" preferred in the present invention, a "functional film" having the function of a semiconductor, in particular, the function of an organic semiconductor is mentioned. The "functional film" having such a function of an organic semiconductor of the present invention has a function to form an organic thin film and excellent insulating properties on one plane of the triptycene skeletal structure, and has the function of an organic semiconductor on the other plane of the triptycene skeletal structure, and thus it is possible to treat the surface of the insulating layer without impairing the insulating properties of the gate insulating layer and to provide an organic thin film having the function of an organic semiconductor on the plane opposite to the insulating layer at the same time. In addition, as has been described above, the organic thin film of the present invention itself has a film forming ability, thus it is possible to form a stable organic thin film without being dependent on the material of the gate insulating layer, and the "functional film" of the present invention can be widely employed to either of an inorganic insulating material or an organic insulating material.

As the "solid substrate" in the present invention, not only a solid substrate such as glass; a non-metal such as silicon or germanium; a nonmetal oxide such as silicon oxide; a metal such as gold, platinum, silver or copper; a metal oxide such as indium oxide or indium tin oxide (ITO); GaAs; or CdS which has been used as a solid substrate for a SAM or the like in the related art but also a solid substrate such as a polycarbonate substrate, a substrate made from a flexible plastic material such as polyether sulfone (PES) or polyethylene terephthalate (PET), an organic insulating material such as polyimide, poly(methyl methacrylate) or poly(p-xylylene) (Parylene (registered trademark)) or the like can be used. In addition, a biological derived material using a material derived from animals and plants such as collagen, starch or cellulose as a raw material can also be used as a solid substrate. As has been described above, the organic thin film of the present invention itself has a film forming ability, thus a solid that a SAM or the like in the related art is hardly bonded to or adsorbed on can also be used as the substrate, and all the solids described above on which the organic thin film of the present invention can stably exist can be included in the solid substrate. Moreover, the shape of the solid is not also particularly limited, and it may have a flexible sheet shape or a thin film shape.

The film using the Janus-type triptycene derivative of the present invention has not only the van der Waals force by the alkyl chains and the like but also film forming ability in the triptycene skeletal structure moiety, and thus it does not necessarily require the moiety for being bonded to or adsorbed on the surface of a solid substrate. Hence, it is not required to consider the bonding properties or the adsorption ability for the solid substrate, and the solid substrate is not particularly limited. However, it is preferable to select a solid substrate which the film using the Janus-type triptycene derivative of the present invention is capable of being bonded to and/or adsorbed on in order to secure positional stability of the film formed.

The "electronic device" in the present invention is a general term for electronic elements to do functional works such as amplification, data processing, and data transfer by applying the action of electrons. Examples of the typical "electronic device" may include an active element such as a transistor, a diode, a thyristor, an organic EL, or a biosensor, but a passive element such as a resistor or a capacitor is also included in some cases. Examples of the electronic device in a preferred aspect of the present invention may include a transistor, in particular, a thin film transistor, and more preferably an organic field-effect transistor (OFET). The organic field-effect transistor (OFET) may be any of a bottom contact/top gate type, a bottom contact/bottom gate type, and a top contact/bottom gate type, but a top contact/bottom gate type is preferred.

The "electronic element" in the present invention is a general term for electronic components utilizing the electronic conduction in solid, includes an active element and a passive element, and may be either of an active element or a passive element in the present invention, but is usually preferably an active element. In addition, the "electronic device" and the "electronic element" of the present invention are used as synonyms in a case in which the electronic device is configured by a single electronic element.

The "circuit board" in the present invention refers to those in which an electronic circuit is formed on the surface of the solid substrate described above. The electronic circuit is an electric circuit to connect an electronic component to an electrical conductor, to create a path of current, and to allow the electric component to perform the intended operation, and the electronic circuit can amplify a signal of interest, perform data processing such as calculation and control, or transfer data. The "circuit board" can have various sizes depending on the purpose. For example, it can be a circuit that performs all of the input, processing, control, and output of data, or it may be a circuit that performs only one of the respective purposes.

The "electronic apparatus" in the present invention includes various kinds of electronic products equipped with at least one kind of the electronic device, electronic element, and circuit board that are described above, and examples thereof may include: electronic products for home use such as a television; a view finder type or monitor direct view type video tape recorder; a car navigation apparatus; an electronic notebook; an electronic calculator; an electronic newspaper; a word processor; a personal computer; a workstation; a TV phone; and a POS terminal, in particular, a display device of these electronic products, and electronic products for business use such as medical electronic apparatuses such as a cardiac potential measuring device, a muscle potential measuring device and a brain potential measuring device, in particular, a display device of these medical electronic apparatuses. In addition, the "electronic apparatus" of the present invention may be various kinds of devices constituting the electronic products described above, and examples of such a device may include a display device such as an electronic paper, an organic EL display, or a liquid crystal display, and a sensor device such as various kinds of sensors.

The "component" in the present invention refers to the part that is required to constitute the electronic devices or electronic elements described above and formed by materials having the same nature. For example, a layer such as an insulating layer or an organic thin film layer is mentioned as the example of the "component". In addition, to include the "component" means that the electronic devices or electronic elements described above include the "component" therein, that is, the "component" is present as a part of the electronic devices or electronic elements described above.

The "divalent saturated or unsaturated hydrocarbon group having from 2 to 60 carbon atoms" in the present invention is a divalent saturated or unsaturated, chain or cyclic, and linear or branched hydrocarbon group having from 2 to 60, preferably from 2 to 30, and more preferably from 5 to 30 carbon atoms. These saturated carbon atoms, unsaturated carbon atoms, carbon atoms forming a chain, and carbon atoms forming a ring may be regularly or irregularly disposed. Examples of the "divalent saturated or unsaturated hydrocarbon group having from 2 to 60 carbon atoms" in the present invention may include a linear or branched alkylene group having from 2 to 60, preferably from 2 to 30, and more preferably from 5 to 20 carbon atoms; a linear or branched alkenylene group having from 2 to 60, preferably from 2 to 30, and more preferably from 2 to 20 carbon atoms; a linear or branched alkynylene group having from 2 to 60, preferably from 2 to 30, and more preferably from 2 to 20 carbon atoms; and a divalent arylene group having from 6 to 60, preferably from 6 to 30 carbon atoms in total which contains a monocyclic, polycyclic, or condensed aryl ring having from 6 to 30, preferably from 6 to 20, and more preferably from 6 to 12 carbon atoms (the arylene group may have an alkylene group, an alkenylene group, or alkynylene group between an aryl ring and another aryl ring or at the end). The carbon-carbon double bond for forming an alkenylene group, the carbon-carbon triple bond for forming an alkynylene group, or an aryl ring for forming an alkylene group may be regularly or irregularly disposed in a saturated alkylene group or an unsaturated alkynylene group.

More specifically, for example, a $C_6$, $C_7$, $C_8$, $C_9$, $C_{10}$, $C_{11}$, $C_{12}$, $C_{13}$, $C_{14}$, $C_{15}$, $C_{16}$, or $C_{17}$ linear or branched and preferably linear alkylene group, an alkylene group in which one, two, or three carbon-carbon double bonds are regularly or irregularly disposed in the alkylene group described above, a —(—CH=CH—)n- unsaturated alkylene group (here, n represents an integer of 3, 4, 5, 6, 7, or 8), an arylene group represented by -(-Ph-CH=CH—)m-Ph- (here, Ph represents a p-phenylene group and m represents an integer of 1, 2, 3, or 4), and the like.

The "divalent saturated or unsaturated hydrocarbon group having from 2 to 60 carbon atoms" in the present invention may optionally have one or more substituents, and examples of the "substituent" may include a substituent selected from the group consisting of a halogen atom; a hydroxyl group; an alkyl group having from 1 to 5 carbon atoms; an alkoxy group having from 1 to 5 carbon atoms; an alkyl group which has from 1 to 5 carbon atoms and is substituted with from 1 to 5 and preferably from 1 to 3 halogen atoms; an alkoxy group which has from 1 to 5 carbon atoms and is substituted with from 1 to 5 and preferably from 1 to 3 halogen atoms; an amino group; and an amino group substituted with one or two alkyl groups having from 1 to 5 carbon atoms.

The description that "one or more carbon atoms in the hydrocarbon group may be optionally substituted with oxygen atom, sulfur atom, silicon atom, or —$NR^5$— (here, $R^5$ represents a hydrogen atom, an alkyl group having from 1 to 10 carbon atoms, or an aryl group having from 6 to 30 carbon atoms)" in the present invention indicates that one or two or more carbon atoms in the chain of carbon atoms of —C—C—C— may be substituted with another atom so as to form a chain, for example, —C—O—C—, —C—S—C—, —C—$SiH_2$—C— (hydrogen atoms bonded to the silicon atom in the formula may be substituted with a halogen atom, an alkyl group having from 1 to 10 carbon atoms or an alkoxy group having from 1 to 10 carbon atoms), or —C—$NR^5$—C—. In such substitution with another atom, the order of the substitutions may be regular or irregular.

Examples of the "alkyl group having from 1 to 10 carbon atoms" in the present invention may include a linear or branched alkyl group having from 1 to 10 carbon atoms, preferably from 1 to 8 carbon atoms, and more preferably from 1 to 5 carbon atoms. Examples of such an alkyl group may include a methyl group, an ethyl group, a n-propyl group, an isopropyl group, a n-butyl group, an isobutyl group, a sec-butyl group, a tert-butyl group, a pentyl group, a hexyl group, and an octyl group.

Examples of the "alkyl group which has from 1 to 5 carbon atoms and may have a substituent" in the present invention may include a linear or branched alkyl group having from 1 to 5 carbon atoms, preferably from 1 to 4 carbon atoms, more preferably form 1 to 3 carbon atoms. Examples of such an alkyl group may include a methyl group, an ethyl group, a n-propyl group, an isopropyl group, a n-butyl group, an isobutyl group, a sec-butyl group, a tert-butyl group, and a pentyl group.

Examples of the "alkenyl group having from 2 to 10 carbon atoms" in the present invention may include a linear or branched alkenyl group that is a group having one or more carbon-carbon double bonds and has from 2 to 10 carbon atoms in total, preferably from 2 to 8 carbon atoms in total, and more preferably from 2 to 6 carbon atoms in total. Examples of such an alkenyl group may include a vinyl group, a 1-methyl-vinyl group, a 2-methyl-vinyl group, a n-2-propenyl group, a 1,2-dimethyl-vinyl group, a 1-methyl-propenyl group, a 2-methyl-propenyl group, a n-1-butenyl group, a n-2-butenyl group, and a n-3-butenyl group.

Examples of the "alkynyl group having from 2 to 10 carbon atoms" in the present invention may include a linear or branched alkynyl group that is a group having one or more carbon-carbon triple bonds and has from 2 to 10 carbon atoms in total, preferably from 2 to 8 carbon atoms in total, and more preferably from 2 to 6 carbon atoms in total. Examples of such an alkynyl group may include an ethynyl group, a n-1-propynyl group, a n-2-propynyl group, a n-1-butynyl, a n-2-butynyl, and a n-3-butynyl group.

Examples of the "aryl group having from 6 to 30 carbon atoms" in the present invention may include a monocyclic, polycyclic, or condensed aryl group having from 6 to 36 carbon atoms, preferably having from 6 to 18 carbon atoms, and more preferably from 6 to 12 carbon atoms. Examples of such a carbocyclic aromatic group may include a phenyl group, a naphthyl group, a biphenyl group, a phenanthryl group, and an anthryl group.

Examples of the "5- to 8-membered heteroaryl group which has from 1 to 5 heteroatoms selected from the group consisting of nitrogen atom, oxygen atom, and sulfur atom and has from 2 to 10 carbon atoms" in the present invention may include a monocyclic, polycyclic, or condensed heteroaryl group which contains from 1 to 5, preferably from 1 to 3 or from 1 to 2 heteroatoms selected from the group consisting of nitrogen atom, oxygen atom, and sulfur atom and has a 5- to 8-membered ring and preferably a 5- to 6-membered ring. Examples of such a heterocyclic group may include a 2-furyl group, a 2-thienyl group, a 2-pyrrolyl group, a 2-pyridyl group, a 2-indole group, and a benzimidazolyl group.

Examples of the "alkoxy group having from 1 to 10 carbon atoms" in the present invention may include a group in which an oxygen atom is bonded to the above-described alkyl group having from 1 to 10 carbon atoms. Examples of such an alkoxy group may include a methoxy group, an ethoxy group, a n-propoxy group, an isopropoxy group, a butoxy group, and a pentyloxy group.

Examples of the "alkylthio group having from 1 to 10 carbon atoms" in the present invention may include a group in which a sulfur atom is bonded to the above-described alkyl group having from 1 to 10 carbon atoms. Examples of such an alkylthio group may include a methylthio group, an ethylthio group, a n-propylthio group, an isopropylthio group, a butylthio group, and a pentylthio group. The sulfur atom in these alkylthio groups may be sulfinyl (—SO—) or sulfonyl (—SO$_2$—).

Examples of the "alkylcarbonyl group having from 1 to 10 carbon atoms" in the present invention may include a group in which a carbonyl group (—CO— group) is bonded to the above-described alkyl group having from 1 to 10 carbon atoms. Examples of such an alkylcarbonyl group may include a methylcarbonyl group, an ethylcarbonyl group, a n-propylcarbonyl group, and an isopropylcarbonyl group.

Examples of the "alkoxycarbonyl group having from 1 to 10 carbon atoms" in the present invention may include a group in which an oxycarbonyl group (—O—CO— group) is bonded to the above-described alkyl group having from 1 to 10 carbon atoms. Examples of such an alkoxycarbonyl group may include a methoxycarbonyl group, an ethoxycarbonyl group, n-propoxycarbonyl group, and an isopropoxycarbonyl group.

Examples of the "alkylcarbonyloxy group having from 1 to 10 carbon atoms" in the present invention may include a group in which a carbonyloxy group (—CO—O— group) is bonded to the above-described alkyl group having from 1 to 10 carbon atoms. Examples of such an alkylcarbonyloxy group may include a methyl carbonyloxy group, an ethylcarbonyloxy group, a n-propylcarbonyloxy group, and an isopropylcarbonyloxy group.

The "substituent" in the various kinds of groups in the present invention is not particularly limited, but examples thereof may include a halogen atom, a hydroxyl group, a nitro group, a cyano group, a substituted or unsubstituted amino group, an alkylsilyl group, an alkyl group having from 1 to 10 carbon atoms, an alkenyl group having from 2 to 10 carbon atoms, an alicyclic hydrocarbon group having from 3 to 10 carbon atoms, an aryl group having from 6 to 30 carbon atoms, an arylalkyl group having from 7 to 30 carbon atoms, a heteroaryl group, an alkylcarbonyl group having from 1 to 10 carbon atoms, an alicyclic hydrocarbon-carbonyl group having from 3 to 16 carbon atoms, an arylcarbonyl group having from 6 to 30 carbon atoms, an arylalkylcarbonyl group having from 7 to 30 carbon atoms, an alkoxy group having from 1 to 10 carbon atoms, an alkylcarbonyloxy group having from 1 to 10 carbon atoms, an arylcarbonyloxy group having from 7 to 30 carbon atoms, an arylalkylcarbonyloxy group having from 7 to 30 carbon atoms, an alkoxycarbonyl group having from 2 to 21 carbon atoms, a carbocyclic aromatic-oxycarbonyl group having from 7 to 37 carbon atoms, an aryloxycarbonyl group having from 6 to 30 carbon atoms, and an arylalkyloxycarbonyl group having from 7 to 30 carbon atoms.

The "monoalkyl-substituted amino group" in the present invention is an amino group in which one hydrogen atom in the amino group (—NH$_2$) is substituted with the above-described alkyl group having from 1 to 10 carbon atoms, and examples thereof may include a methylamino group and an ethylamino group.

The "dialkyl-substituted amino group" in the present invention is an amino group in which two hydrogen atoms in the amino group (—NH$_2$) are substituted with the above-described alkyl group having from 1 to 10 carbon atoms, respectively, and examples thereof may include a dimethylamino group, a diethylamino group, and a methylethylamino group.

The "formyl group" in the present invention is an aldehyde group (—CHO).

Examples of the "halogen atom" in the present invention may include fluorine atom, chlorine atom, bromine atom, or iodine atom.

The "trialkylsilyl group" in the present invention is a silyl group substituted with three of the above-described alkyl group having from 1 to 5 carbon atoms, and the respective alkyl groups may be the same as or different from one another. Examples of such a trialkylsilyl group may include a triethylsilyl group, an ethyldimethylsilyl group, a tert-butyldimethylsilyl group, and a tert-butyldiethylsilyl group.

The "linker group consisting of a divalent atomic group composed of from 1 to 5 atoms selected from the group consisting of nitrogen atom, oxygen atom, sulfur atom, carbon atom, and silicon atom, and one or more hydrogen atoms if necessary" in the divalent linker group X of Formula [I] of the present invention is a group consisting of a divalent atomic group composed of from 1 to 5 atoms selected from the group consisting of nitrogen atom, oxygen atom, sulfur atom, carbon atom, and silicon atom other than hydrogen atom, and one or more hydrogen atom if necessary, and is a group to link the triptycene skeletal structure with the group $R^1$ of a divalent hydrocarbon group, and the structure of the linker group is not particularly limited. Preferred examples of the group X may include —O—; —S—; —SO—; —SO$_2$—; —NR$^6$— (here, $R^6$ represents a hydrogen atom or an alkyl group having from 1 to 4 carbon atoms); —CH$_2$—; —CH$_2$—CH$_2$—; —CH=CH—; —C$_6$H$_4$— (phenylene group); —C$_4$H$_2$S— (divalent thiophene); —CO—; —OCO—; —COO—; —OCOO—; —CONR$^{61}$— (here, $R^{61}$ represents a hydrogen atom or an alkyl group having from 1 to 3 carbon atoms); —NR$^{62}$CO— (here, $R^{62}$ represents a hydrogen atom or an alkyl group having from 1 to 2 carbon atoms); —NHCONH—, —CO—NR$^{63}$—NR$^{63}$— (here, $R^{63}$ each independently represent a hydrogen atom or a methyl group); —SiR$^9$R$^{10}$—O— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl group having from 1 to 3 carbon atoms); —O—SiR$^9$R$^{10}$—O— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl groups having from 1 to 3 carbon atoms); —SiR$^9$R$^{10}$—NH— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl groups having from 1 to 3 carbon atoms); and —NH—SiR$^9$R$^{10}$— (here, $R^9$ and $R^{10}$ each independently represent a hydrogen atom, an alkyl group having from 1 to 3 carbon atoms, an alkoxy group having from 1 to 3 carbon atoms, or an amino group which may be substituted with an alkyl groups having from 1 to 3 carbon atoms).

Preferred examples of the group X in Formula [I] may include —O—; —S—; —SO—; —SO$_2$—; —NR$^6$— (here, $R^6$ represents a hydrogen atom or an alkyl group having from 1 to 4 carbon atoms); —CH$_2$—; —CO—; —OCO—; —CONR$^{61}$— (here, $R^{61}$ represents a hydrogen atom or an alkyl group having from 1 to 3 carbon atoms); and —NR$^{62}$CO— (here, $R^{62}$ represents a hydrogen atom and or an alkyl group having from 1 to 2 carbon atoms), and particularly preferred examples of the group X may include —O—; —NR$^6$— (here, $R^6$ represents a hydrogen atom or an alkyl group having from 1 to 4 carbon atoms); —CH$_2$—; and —CO—.

The "group capable of being bonded to or adsorbed on the surface of a solid substrate" in the end group Z in Formula [I] of the present invention is a functional group that can be bonded to or adsorbed on the surface of a substrate such as glass, a metal, or a metal oxide, and examples thereof may include a trimethoxysilyl group or a trichlorosilyl group with respect to a glass substrate, and a group containing a sulfur atom such as a mercapto group or a disulfide group with respect to gold.

The "end group consisting of a monovalent atomic group composed of from 1 to 15 atoms selected from the group consisting of nitrogen atom, oxygen atom, sulfur atom, carbon atom, phosphorus atom, and silicon atom, and one or more hydrogen atoms if necessary" in the end group Z in Formula [I] of the present invention is a monovalent group to be the end of the group $R^1$ of a divalent hydrocarbon group in Formula [I] of the present invention and is not particularly limited as long as it is a monovalent atomic group composed of from 1 to 15, preferably from 1 to 10, and more preferably from 1 to 6 atoms and one or more hydrogen atoms if necessary. Preferred examples of the group Z may include an alkyl group having from 1 to 10 carbon atoms; a linear or branched alkenyl group having from 2 to 15, preferably from 2 to 10, and more preferably from 2 to 6 carbon atoms; a linear or branched alkynyl group having from 2 to 15, preferably from 2 to 10, and more preferably from 2 to 6 carbon atoms; a divalent aryl group having from 6 to 15, and preferably from 6 to 12 carbon atoms in total which contains a monocyclic, polycyclic, or condensed aryl ring having from 6 to 15, preferably from 6 to 12, and more preferably 6 to 10 carbon atoms (the aryl group may have an alkylene group, an alkenylene group, or an alkynylene group between an aryl ring and another aryl ring or at the end); a haloalkyl group having from 1 to 10 carbon atoms in which any position of an alkyl group having from 1 to 10 carbon atoms is substituted with from 1 to 7 halogen atoms; —OR$^{11}$ (here, $R^{11}$ represents a hydrogen atom or an alkyl group having from 1 to 10 carbon atoms); —SR$^{11}$ (here, $R^{11}$ represents a hydrogen atom or an alkyl group having from 1 to 10 carbon atoms); —SOR$^{11}$ (here, $R^{11}$ represents a hydrogen atom or an alkyl group having from 1 to 10 carbon atoms); —SO$_2$R$^{11}$ (here, $R^{11}$ represents a hydrogen atom or an alkyl group having from 1 to 10 carbon atoms); —N(R$^{12}$)$_2$ (here, $R^{12}$'s each independently represent a hydrogen atom, an alkyl group having from 1 to 10 carbon atoms or an aryl group having from 6 to 12 carbon atoms); —CO—R$^{13}$ (here, $R^{13}$ represents a hydrogen atom, an alkyl group having from 1 to 10 carbon atoms or an aryl group having from 6 to 12 carbon atoms); —OCO—R$^{13}$ (here, $R^{13}$ represents a hydrogen atom, an alkyl group having from 1 to 10 carbon atoms or an aryl group having from 6 to 12 carbon atoms); —COO—R$^{13}$ (here, $R^{13}$ represents a hydrogen atom, an alkyl group having from 1 to 10 carbon atoms or an aryl group having from 6 to 12 carbon atoms); —OCOO—R$^{14}$ (here, $R^{14}$ represents an alkyl group having from 1 to 10 carbon atoms or an aryl group having from 6 to 12 carbon atoms); —CON(R$^{13}$)$_2$ (here, $R^{13}$'s each independently represent a hydrogen atom, an alkyl group having from 1 to 10 carbon atoms or an aryl group having from 6 to 12 carbon atoms); —NR$^{13}$CO—R$^{13}$ (here, $R^{13}$'s each independently represent a hydrogen atom, an alkyl group having from 1 to 10 carbon atoms or an aryl group having from 6 to 12 carbon atoms; —N(R$^{13}$)CON(R$^{13}$)$_2$ (here, $R^{13}$'s each independently represent a hydrogen atom, an alkyl group having from 1 to 10 carbon atoms or an aryl group having from 6 to 12 carbon atoms); —CO—NR$^{13}$—N(R$^{13}$)$_2$ (here, $R^{13}$'s each independently represent a hydrogen atom, an alkyl group having from 1 to 10 carbon atoms or an aryl group having from 6 to 12 carbon atoms); —SiR$^9$R$^{10}$—O—R$^{13}$ (here, $R^9$ and $R^{10}$ each independently represent a hydrogen atom, an alkyl group having from 1 to 3 carbon atoms, an alkoxy group having from 1 to 3 carbon atoms, or an amino group which may be substituted with one or more alkyl groups having from 1 to 3 carbon atoms, and $R^{13}$ represents a hydrogen atom, an alkyl group having from 1 to 10 carbon atoms or an aryl group having from 6 to 12 carbon atoms); —O—$SiR^9R^{10}$—O—$R^{13}$ (here, $R^9$ and $R^{10}$ each independently represent a hydrogen atom, an alkyl group having from 1 to 3 carbon atoms, an alkoxy group having from 1 to 3 carbon atoms, or an amino group which may be substituted with one or more alkyl group having from 1 to 3 carbon atoms, and $R^{13}$ represents a hydrogen atom, an alkyl group having from 1 to 10 carbon atoms or an aryl group having from 6 to 12 carbon atoms); —$SiR^9R^{10}$—$N(R^{13})_2$ (here, $R^9$ and $R^{10}$ each independently represent a hydrogen atom, an alkyl group having from 1 to 3 carbon atoms, an alkoxy group having from 1 to 3 carbon atoms, or an amino group which may be substituted with one or more alkyl group having from 1 to 3 carbon atoms, and $R^{13}$ represents a hydrogen atom, an alkyl group having from 1 to 10 carbon atoms or an aryl group having from 6 to 12 carbon atoms); —NH—$SiR^9R^{10}$—O—$R^{13}$ (here, $R^9$ and $R^{10}$ each independently represent a hydrogen atom, an alkyl group having from 1 to 3 carbon atoms, an alkoxy group having from 1 to 3 carbon atoms, or an amino group which may be substituted with one or more alkyl group having from 1 to 3 carbon atoms, and $R^{13}$ represents a hydrogen atom, an alkyl group having from 1 to 10 carbon atoms or an aryl group having from 6 to 12 carbon atoms); —$P(OR^{15})_2$ (here, $R^{15}$'s each independently represent a hydrogen atom, an alkyl group having from 1 to 10 carbon atoms or an aryl group having from 6 to 12 carbon atoms); and —$P(=O)(OR^{15})_2$ (here, $R^{15}$'s each independently represent a hydrogen atom, an alkyl group having from 1 to 10 carbon atoms or an aryl group having from 6 to 12 carbon atoms).

The "Janus-type triptycene derivative" of Formula [I] of the present invention is a triptycene derivative which has two different planes of the plane on positions of 1, 8, and 13 and the plane on positions of 4, 5, and 16 and of which the two different planes have properties different from each other. As the method of producing a triptycene derivative of the related art, a triptycene derivative is produced by the Diels-Alder reaction using benzoquinone as a key reaction, but it is difficult to produce the "Janus-type triptycene derivative" of the present invention by this method since the same substituent (—OH) is simultaneously introduced into the 13-position and the 16-position.

The present inventors have succeeded in producing a three substituted triptycene derivative by conducting the condensation of a compound in which a phenolic hydroxyl group of 1-alkoxy-6-trialkylsilyl-phenol is set as the leaving group by a triflate group and 1,8-dialkoxyanthracene in the presence of a condensing agent. A specific example of this reaction is presented in Production Examples to be described later. It is possible to produce a three substituted triptycene derivative by this method, but the three substituted triptycene derivative thus produced is a mixture of a 1,8,13-three substituted triptycene derivative (Janus type) and a 1,8,16-three substituted triptycene derivative (non-Janus type), thus it is difficult to separate the mixture, but the present inventors have succeeded in separating and purifying the 1,8,13-trimethoxytriptycene by purifying this through recrystallization. See Production Examples to be described later.

The 1,8,13-trimethoxytriptycene can be separated and purified as a crystal having a unique packing structure in which the benzene rings arranged in a three-blade shape of the triptycene site are integrated in a nesting shape. This crystal structure has an integrated structure in which the dipole is offset in the layer of triptycene molecule having a methoxy group and the layer of triptycene molecule having no methoxy group. Surprisingly, such a nesting-shaped crystal structure is not seen in the non-substituted triptycene. It is also demonstrated in this crystal structure that the characteristic integrated structure is brought about by the substituent structure of the Janus-type molecule of the present invention furnished with directionality.

This crystal form is an orthorhombic crystal system, and the values of a, b, and c of this crystal form are 15.608, 13.388, and 8.041, respectively, in a unit of angstrom. The value of V is 1680 cubic angstrom.

As described above, the present inventors have succeeded for the first time in producing a "Janus-type triptycene derivative" having the same substituent in one direction of the triptycene skeletal structure.

The 1,8,13-trimethoxytriptycene that is separated and purified in this manner can be converted into 1,8,13-trihydroxytriptycene through hydrolysis by a usual method. For example, 1,8,13-trimethoxytriptycene can be hydrolyzed in a solvent such as dichloromethane in the presence of a boron halide.

Moreover, it is possible to produce the "Janus-type triptycene derivative" of the present invention and an intermediate compound thereof by various kinds of known synthetic means using 1,8,13-trimethoxytriptycene and 1,8,13-trihydroxytriptycene obtained by the hydrolysis thereof as the key intermediate.

For example, 1,8,13-trihydroxytriptycene can be converted into a trialkoxy derivative through alkylation using an alkylating agent. In addition, they can be converted into an ester derivative by various kinds of carboxylic acids or sulfonic acids. Furthermore, they can be converted into 1,8,13-tricyanotriptycene by substituting the hydroxyl group with triflate (Tf: trifluoromethanesulfonate) and then cyanating with zinc cyanide. The cyano group can be converted into a formyl group or a carboxyl group through hydrolysis by a usual method. In addition, the cyano group can be converted into an aminomethyl group through reduction by a usual method, and the amino group can be substituted with various kinds of substituents by a usual method.

In addition, the formyl group thus obtained can be used as various kinds of reaction raw materials as a carbonyl compound. For example, the formyl group can be converted into a —CH=C— bond through a reaction with a Wittig reagent. This can be converted into a carbon-carbon triple bond through dehydrogenation by a usual method.

Furthermore, it is possible to produce 4,5,16-tribromo-1,8,13-trihydroxytriptycene by the bromination of 1,8,13-trihydroxytriptycene using NBS (N-bromosuccinimide). This compound is a compound that has different substituents of three hydroxyl groups on one side and three bromo groups on the other side of the symmetry plane in the triptycene molecule and is a compound that is a key intermediate of the "Janus-type triptycene derivative" of the present invention having different groups having functions with respect to one symmetry plane.

This bromo-containing derivative can be directly converted into various kinds of aryl groups or heteroaryl groups such as a phenyl group or a thienyl group through various kinds of coupling reactions using a boron compound or a silicon compound. For example, in the case of attempting to introduce a group having a function to be an electron acceptor on the side where the bromo group is substituted, the group having a function can be introduced directly or stepwise by such coupling reactions.

The compound represented by Formula [I] of the present invention is characterized by having different substituents on two planes of the plane on positions of 1, 8, and 13 and the plane on positions of 4, 5, and 16 of the triptycene and having three identical substituents on at least either of the two planes. Moreover, the compound represented by Formula [I] of the present invention is characterized in that such a unique triptycene derivative forms a unique packing structure in which the benzene rings arranged in a three-blade shape of the triptycene site are integrated in a nesting shape and thus can form a unique organic thin film. Furthermore, the present invention is characterized in that an organic thin film containing a triptycene derivative having such a unique structure is used as a component of an electronic device.

The method of producing the Janus-type triptycene derivative represented by Formula [I] of the present invention has a great characteristic that 1, 8, 13-trimethoxytriptycene which is successfully separated and purified by the present inventors for the first time is adopted as a key intermediate, and it is easily understood by those skilled in the art that various kinds of Janus-type triptycene derivatives of the present invention can be produced from 1, 8, 13-trimethoxytriptycene by combining with a usual synthetic means.

In the case of producing a compound represented by Formula [I] of the present invention, the compound can be produced by first producing a compound represented by the following Formula [III]:

$$Y^1-R^1-Z \qquad [III]$$

(in Formula [III], $R^1$ and Z represent the group described above, $Y^1$ represents a leaving group such as halogen) by a known method and then reacting this with a 1,8,13-three substituted triptycene derivative. This reaction is a substitution reaction and can be conducted according to various kinds of known substitution reactions.

In addition, in a case in which the substituent Z is reactive, it is possible to conduct the substitution reaction after protecting Z with various kinds of protecting groups, or to conduct the substitution reaction using a compound having a precursor of Z, for example, a compound having a cyano group in a case in which the substituent Z is a carboxyl group and then to hydrolyze a product obtained into a compound having a substituent Z. In a case in which Z is an ester group, the substitution reaction may be conducted without protecting Z, or the substitution reaction and the hydrolysis may be conducted to obtain a compound having a carboxyl group and then the carboxyl group is esterified. Although the protective group and the deprotection are well known to those skilled in the art, see Protective Group in Organic Synthesis (John Wiley and Sons, 1991) written by T. W. Green, if necessary.

In addition, in a case of a compound in which the substituent of the 1,8,13-three substituted triptycene derivative is a carbonyl group such as a formyl group, it is possible to produce a compound of Formula [I] in which the group X is —C=C— by using a Wittig reagent.

For example, it is possible to produce Compound 1 having the ester group as an end group described above by reacting 1,8,13-trihydroxytriptycene as a raw material with methyl 12-bromododecanoate (it may be chloro, iodo, or a pseudo-halide such as a tosylate ester instead of bromo) by the Williamson synthesis reaction in the presence of a base.

It is possible to use a solvent in these reactions if necessary. Examples of such a solvent may include a ketone-based solvent such as acetone or methyl ethyl ketone, an ether-based solvent such as diethyl ether or THF, an aprotic polar solvent such as DMF, DMA, or DMSO, an alcohol-based solvent such as ethanol, an aromatic hydrocarbon-based solvent such as toluene or xylene, and a halogen-based solvent such as dichloromethane or chlorobenzene, but the solvent is not limited thereto. In addition, it is also possible to conduct the reaction in the presence of various kinds of reagents if necessary. A base is preferred as such a reagent, and examples of the base may include an alkali metal carbonate such as potassium carbonate, sodium carbonate or cesium carbonate, and an alkali metal hydroxide such as sodium hydroxide or potassium hydroxide, but the base is not limited thereto. It is also possible to use an organic base such as a trialkylamine as the base, but an inorganic base is preferred.

The reaction temperature can be arbitrarily set as long as the reaction properly proceeds, but the temperature is usually preferably in the range of from room temperature to the boiling point of the solvent. As the method to isolate the intended product from the reaction mixture and to purify it, a usual isolation and purification means, for example, a method such as solvent extraction, recrystallization, reprecipitation, silica gel column chromatography, or gel filtration chromatography can be conducted. In addition, in a case in which the product is optically active, the optical resolution thereof can also be conducted if necessary.

In the Janus-type triptycene derivative represented by Formula [I] of the present invention, the benzene rings arranged in three-blade shape of triptycene are integrated in a nesting shape, and thus it is possible to reasonably construct a two-dimensional molecular assembly with controlled dimensionality and to form an organic thin film by utilizing such a characteristic integration behavior. As the method of producing the film of the present invention, it is possible to arbitrarily select a spin coating method, a dipping method, a casting method, an ink jet method, an ultrasonic method, a vapor phase method, a vapor deposition method or the like, but a spin coating method, a dipping method, a casting method, an ink jet method, a vapor deposition method or the like is preferred since the compound of the present invention can be dissolved in an organic solvent.

The spin coating method is a method to form a thin film having a uniform film thickness by dropping a solution on a substrate rotating at a high speed. The dipping method is a method to form a film by immersing a substrate in a solution. The casting method (including drop casting) is a method to form a film by dropping a solution on a substrate and then drying the solvent, but the film thickness of the film is not always uniform. The inkjet method is a method to form a film by dropping a trace amount of solution at an arbitrary position. In addition, as the method of producing the film of the present invention, it is possible to form a film by these known film forming methods, but it is also possible to form a film by a film forming method at a liquid/liquid interface since the film of the present invention exhibits a unique integration behavior. For example, it is also possible to bring a solution prepared by dissolving the compound of the present invention in an organic solvent which does not dissolve in water into contact with water to form an interface of water/organic solvent and to produce a film at the interface. The organic thin film thus produced can also be used as a component of an electronic device and the like.

In addition, some of the compounds among the compounds represented by Formula [I] of the present invention can be formed into a film by a vapor deposition method and preferably a vacuum deposition method. In particular, a compound which has a relatively low melting point and a high decomposition temperature is preferred. The vapor deposition method in the present invention can be conducted by a usual vapor deposition method. For example, it is preferable that the compound is evaporated by heating to the melting point or higher of the compound or the compound is sublimated in a case in which the compound is sublimable, and then the vapor deposition is conducted under the reduced pressure of from $10^{-5}$ Pa to $10^{-3}$ Pa. The temperature of the substrate may be in the vicinity of room temperature, but it is preferably about from 50° C. to 100° C. Examples of the compound of the present invention that is suitable for forming a film by a vapor deposition method may include compounds of Formula [I] in which X is —CH$_2$—, Z is a hydrogen atom, R$^1$ is an alkylene group having from 8 to 15 carbon atoms and preferably an alkylene group having from 9 to 12 carbon atoms.

It is possible to use the solid substrate of the present invention that has been described above in the case of producing the film of the present invention on a solid substrate. Furthermore, it is also possible to adopt a solid substrate prepared by subjecting these solid substrates to a cleaning treatment by ultraviolet light (UV), ozone or the like; and a layered body prepared by layering a connecting terminal such as wiring or an electrode or another layer such as an insulating layer or a conductive layer on these solid substrates as the solid substrate. As the solid substrate used in the present invention, an organic or inorganic insulating material is particularly preferred and an organic insulating material is particularly preferred in an electronic device such as a thin film transistor.

Examples of the method of producing the film of the present invention on a solid substrate may include a method including a process of preparing a solution by dissolving the Janus-type triptycene derivative represented by Formula [I] of the present invention in an organic solvent, subsequently, a process of coating or spin coating the solution on a solid substrate or immersing the solid substrate in the solution, and a process of drying the solution on the solid substrate.

In addition, examples of the method of producing the film of the present invention at an interface may include a method including a process of preparing a solution by dissolving the Janus-type triptycene derivative represented by Formula [I] of the present invention in an organic solvent which is non-miscible with a second solvent such as water, subsequently, a process of forming an interface by adding the second solvent such as water to the solution and forming a film at the interface, a process of separating the film thus produced, and a process of drying the film thus separated.

The film thickness of the film of the present invention produced by such a method is not particularly limited, but the average thickness in the case of a monolayer is from 0.1 nm to 5 nm and preferably from 1 nm to 3 nm. In addition, the average thickness in the case of a multilayer film is from 2 nm to 50 nm and preferably from 3 nm to 30 nm. Furthermore, it is possible to produce a film having a great film thickness in the case of producing a film at a liquid/liquid interface, and it is also possible to have a film thickness of from 30 nm to 1000 nm and preferably from 50 nm to 500 nm.

The organic solvent used when producing the film is not particularly limited as long as it can dissolve the Janus-type triptycene derivative represented by Formula [I] of the present invention, and examples thereof may include a lactone such as γ-butyrolactone; a ketone such as acetone, methyl ethyl ketone, cyclohexanone, methyl-n-amyl ketone, methyl isoamyl ketone, or 2-heptanone; a monohydric alcohol such as methanol, ethanol, or isopropanol; a polyhydric alcohol such as ethylene glycol, diethylene glycol, propylene glycol, or dipropylene glycol, and any derivatives thereof; a glycol ester such as ethylene glycol monoacetate, diethylene glycol monoacetate, propylene glycol monoacetate, or dipropylene glycol monoacetate; a mono ether such as monomethyl ether, monoethyl ether, monopropyl ether, monobutyl ether of the polyhydric alcohol or the ester or a mono ether ester; an ester such as methyl lactate, ethyl lactate (EL), methyl acetate, ethyl acetate, butyl acetate, methyl pyruvate, ethyl pyruvate, methyl methoxypropionate, or ethyl ethoxypropionate; an aromatic organic solvent such as anisole, ethyl benzyl ether, cresyl methyl ether, diphenyl ether, dibenzyl ether, phenetole, butylphenyl ether, ethylbenzene, diethylbenzene, amylbenzene, isopropylbenzene, toluene, xylene, cymene, or mesitylene; a cyclic ether such as dioxane or THF; an amide such as dimethylformamide (DMF) or dimethylacetamide (DMA); and a sulfur-containing solvent such as dimethyl sulfoxide (DMSO). These organic solvents may be used singly or as a mixed solvent of two or more kinds thereof.

Preferred examples of the organic solvent may include an amide such as dimethylformamide (DMF) or dimethylacetamide (DMA), a cyclic ether such as dioxane or THF, and a sulfur-containing solvent such as dimethyl sulfoxide (DMSO). Particularly preferred examples of the solvent may include a polar solvent such as dimethylformamide (DMF) or tetrahydrofuran (THF).

The amount of the organic solvent used is not particularly limited, and the amount may be appropriately set in consideration of the thickness of the film to be produced and the conditions for production. In the case of using drop casting or ink jet, the concentration of solid content is adjusted so as to obtain the intended film thickness in consideration of the area in which the solvent spreads out. At this time, the concentration of the Janus-type triptycene derivative represented by Formula [I] of the present invention in 100 mL of an organic solvent is preferably from 0.01 mg to 1000 mg, more preferably from 0.1 mg to 100 mg, and still more preferably from 0.1 mg to 10 mg.

As described above, it is possible to produce an organic thin film forming composition containing the Janus-type triptycene derivative represented by Formula [I] of the present invention and an organic thin film forming carrier by mixing or dissolving the Janus-type triptycene derivative represented by Formula [I] in an organic thin film forming carrier such as the organic solvent described above.

As the temperature when producing the organic thin film of the present invention, the production can be usually performed at room temperature but can also be performed under heating or cooling depending on the kind of the solvent or the conditions for production.

As the drying in the production of the organic thin film of the present invention, natural drying is sufficient, but the organic thin film can also be dried by a method of blowing dry air, nitrogen or the like or by heating and reducing the pressure if necessary.

In addition, after formation of the film, cleaning of the organic thin film thus produced may be conducted using an organic solvent such as methanol or chloroform or purified water, but it is not particularly required to clean the organic thin film.

In the case of producing the organic thin film of the present invention at an interface, the film produced at the interface can be separated by transferring the film to a substrate such as a glass substrate. The film thus separated can be dried by the method described above.

The organic thin film of the present invention produced in this manner may be further subjected to an annealing treatment.

The annealing treatment for the film that is produced by a spin coating method, a dipping method, a casting method, an inkjet method or the like is conducted by heating at approximately the same temperature as the melting point of the Janus-type triptycene derivative represented by Formula [I] of the present invention, preferably about from 100° C. to 230° C., more preferably about from 130° C. to 230° C., and still more preferably about from 150° C. to 200° C.

In addition, the annealing treatment for the film that is produced by a vapor deposition method is conducted by heating at about from 100° C. to 200° C. and preferably about from 110° C. to 150° C.

The annealing treatment can be usually conducted in the air, but it may be conducted in an inert gas stream such as a nitrogen stream. The annealing time is not particularly limited, but it is sufficient to conduct the annealing treatment for usually from 5 minutes to 50 minutes and preferably about from 10 minutes to 30 minutes.

The detailed mechanism of the annealing treatment is unknown, but it is believed that the film once formed is reconstructed by annealing so as to have a more uniform film thickness.

The organic thin film of the present invention can be formed to have a single-layer structure or a bilayer structure in which the end groups Z face each other between the molecules depending on the kind of the end group Z in Formula [1]. In addition, it is also possible to adjust the thickness of the organic thin film by the production method and to form an organic thin film that is suitable for a wide range of applications as an electronic material, an optical material, a surface treatment material and the like.

In addition, it is possible to impart hydrophobicity to the surface of the organic thin film formed by the Janus-type triptycene derivative represented by Formula [I] of the present invention so as to improve the affinity of the organic thin film with a hydrophobic substance such as an organic semiconductor. For example, when the contact angle of a water droplet on poly(p-xylylene) that is used as a general purpose organic insulating layer is measured, the contact angle in the case of only poly(p-xylylene) is about 87 degrees, but the contact angle of a water droplet is about 103 degrees in a case in which the organic thin film of the Janus-type triptycene derivative represented by Formula [I] of the present invention is formed on the surface of poly(p-xylylene), and thus it has been revealed that the hydrophobicity of the surface is improved.

The electronic device of the present invention can be manufactured in accordance with a method of manufacturing an electronic device of the related art, at that time, the electronic device of the present invention can be manufactured using the organic thin film of the present invention that has been described above instead of an organic thin film, in particular, a SAM of the related art. As has been described above, the organic thin film of the present invention is not dependent on the substrate, and thus it is possible to form an intended organic thin film on various kinds of organic or inorganic substrates by the method that has been described above.

The production example of a thin film transistor may include a method to be described below.

Aluminum is deposited on a silicon wafer, patterned, and subsequently incinerated in an oxygen plasma to have a surface of aluminum oxide, and then an $Al_2O_3$/Al gate electrode having an insulating layer of aluminum oxide is patterned. A solution of the Janus-type triptycene derivative represented by Formula [I] of the present invention is drop-casted thereon and dried. The annealing treatment may be conducted at about 200° C. if necessary. An organic thin film containing the Janus-type triptycene derivative represented by Formula [I] of the present invention is formed on the patterned $Al_2O_3$/Al gate electrode in this manner. Subsequently, an organic semiconductor such as DNTT (dinaphthothienothiophene) is deposited on the $Al_2O_3$/Al gate electrode and the organic thin film to form an organic semiconductor layer. Thereafter, gold is deposited on the organic semiconductor layer by a vacuum deposition method to form a source electrode and a drain electrode.

In the above method, it is also possible to form a capacitor by directly depositing gold on the organic thin film without forming an organic semiconductor layer.

The capacitor of the present invention is characterized by having a dielectric layer consisting of the organic thin film of the present invention that has been described above between the electrodes. The capacitor of the present invention can also further contain a second dielectric in the dielectric layer. The second dielectric is not particularly limited as long as it is a dielectric used in a capacitor, but an organic dielectric is preferred. In addition, the dielectric layer preferably has a layered structure in the case of containing a second dielectric.

In addition, in the case of manufacturing an electronic paper, first, a transparent and flexible polymer substrate such as a polycarbonate substrate is cleaned, and subsequently a pattern is formed on the substrate using an organic conductive material such as PEDOT (polyethylenedioxythiophene) or metal fine particles such as copper to form a gate electrode. Next, a layer of an organic insulator such as a polyimide, poly(methyl methacrylate), or poly(p-xylylene) is formed on a part or the entire surface of the substrate. Next, an organic thin film containing the Janus-type triptycene derivative represented by Formula [I] of the present invention is formed so as to overlap with the gate electrode. Furthermore, an organic semiconductor such as DNTT (di-naphthothienothiophene) is deposited thereon to form an organic semiconductor layer. Thereafter, gold is deposited on the organic semiconductor layer by a vacuum deposition method or the like to form a source electrode and a drain electrode.

Examples of the insulator in these thin film transistors may include various insulators such as an inorganic material, an organic material, or an organic low-molecular amorphous material. Examples of the inorganic material may include a single-metal oxide such as $SiO_2$, $Al_2O_2$, $Ta_2O_5$, or $ZrO_2$, a composite oxide such as strontium titanate or barium strontium titanate, a nitride such as SiNx, an oxynitride, or a fluoride. Examples of the organic material may include polyimide, poly(methyl methacrylate), poly(p-xylylene), polyvinylphenol, poly(methyl methacrylate), polystyrene, benzocyclobutene, cyanoethyl pullulan, polyvinylidene fluoride, a vinylidene-tetrafluoroethylene copolymer, and other polymer materials. Examples of the organic low-molecular amorphous material may include cholic acid and methyl cholate.

As the method of forming these insulators, it is possible to adopt various film forming methods such as vapor deposition, sputtering, plasma CVD (Chemical Vapor Deposition), anodic oxidation of the gate electrode, coating, and attachment from a solution depending on the material of the insulator. The thickness of the gate insulating layer can be from about 10 nm to about 500 nm although it also depends on the material.

Examples of the semiconductor in these thin film transistors may include an organic semiconductor material or an inorganic oxide semiconductor material. As the organic semiconductor material, it is possible to use a polymer organic semiconductor material such as a polythiophene, polyallylamine, a fluorine-bithiophene copolymer, poly(thienylene vinylene), poly(alkyl thiophene), and any derivative thereof; a low molecular organic semiconductor material such as DNTT (dinaphthothienothiophene), oligothiophene, pentacene, tetracene, copper phthalocyanine, perylene, and any derivative thereof. In addition, it is also possible to use a carbon compound such as carbon nanotubes or a fullerene, a semiconductor nanoparticle dispersion or the like as a material for the semiconductor layer. These organic semiconductor materials can be used as an ink-like solution or a dispersion by being dissolved or dispersed in an aromatic solvent such as toluene. In addition, these organic semiconductor materials can also be formed into a film by a vapor deposition method. Examples of the oxide semiconductor material may include an oxide containing one or more kinds of elements among zinc, indium, tin, tungsten, magnesium, and gallium. Examples of the oxide semiconductor material may include known materials such as zinc oxide, indium oxide, indium zinc oxide, tin oxide, tungsten oxide, and indium gallium zinc oxide (In—Ga—Zn—O), but the oxide semiconductor material is not limited to these materials. The structure of these materials may be any of a monocrystalline structure, a polycrystalline structure, a microcrystalline structure, a mixed crystalline structure of crystalline/amorphous, a structure having a nanocrystal interspersed within an amorphous matrix, and an amorphous structure.

Examples of the substrate in these thin film transistors may include a flexible plastic material such as polyethylene terephthalate (PET), polyimide, polyether sulfone (PES), polyethylene naphthalate (PEN), poly(methyl methacrylate), or polycarbonate; a glass substrate such as quartz; a silicon wafer; and an aluminum wafer.

In addition, the thin film transistor can be provided with a sealing layer and a light shielding layer if necessary. It is possible to select and use a material from the same materials as the materials for the insulator as the material for the sealing layer, and to use those which are prepared by dispersing a light shielding material such as carbon black in a gate material as the light shielding layer.

As apparent from the examples described above, the organic thin film of the present invention can be a component of an electronic device, and this makes it possible to obtain an electron device excellent in stability. In other words, the present invention is to provide an electronic device material including an organic thin film containing the Janus-type triptycene derivative represented by Formula [I] of the present invention.

In addition, it is provided a method of manufacturing the electronic device of the present invention which is characterized by providing an organic thin film containing the Janus-type triptycene derivative represented by Formula [I] of the present invention in an electronic device.

It is possible to form an electronic circuit responding to the purpose such as amplification or data processing by appropriately combining the electronic devices or electronic elements of the present invention to be manufactured in this manner and wiring them on a substrate by a usual method. The electronic circuit formed on a substrate in this manner is a circuit board of the present invention. The circuit board of the present invention may be one sheet or may be formed as plural sheets of two or more depending on the purpose.

Furthermore, it is possible to manufacture the electronic apparatus of the present invention by appropriately combining such circuit boards. The electronic apparatus of the present invention itself may be various kinds of electronic products or may be a device forming a part of the electronic product, for example, a device such as a display device.

Hereinafter, the present invention will be described more specifically with reference to Production Examples and Examples, but the present invention is not limited by these Production Examples and Examples in any way.

Production Example 1 Production of trimethoxytriptycene Mixture Presented Below

[Chemical Formula 4]

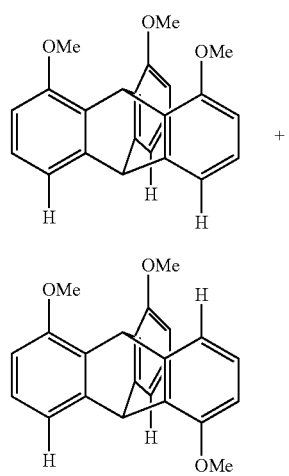

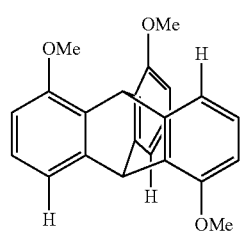

A suspension was prepared by adding acetonitrile (750 mL) to 1,8-dimethoxyanthracene (22.3 g, 93.7 mmol) and cesium fluoride (CsF) (85.3 mg, 561.0 mmol) and heated to 80° C. To this suspension, 2-methoxy-6-trimethylsilyloxy-trifluoromethylsulfonate (61.5 g, 188 mmol) was added dropwise, and the mixture was refluxed while heating for 5 hours. Acetonitrile was distilled off from the reaction mixture thus obtained under reduced pressure, the residue was washed with water and then a mixed solvent of hexane/chloroform (1/1, v/v), thereby obtaining intended trimethoxytriptycene (yield: 22.2 g, 64.5%). The trimethoxytriptycene thus obtained was revealed to be a mixture of 1,8,13-trimethoxytriptycene (Compound 5a) and 1,8,16-trimethoxytriptycene (Compound 5b) of 2:1 by the NMR measurement.

Compound 5a:

$^1$H-NMR (400 MHz, CDCl$_3$): δ(ppm)

7.01 (d, J=0.7 Hz, 3H), 6.90 (dd, J=7.3, 1.0 Hz, 3H), 6.80 (s, 1H), 6.58 (dd, J=8.2, 0.7 Hz, 3H), 5.38 (s, 1H), 3.86 (s, 9H).

Compound 5b:

$^1$H-NMR (400 MHz, CDCl$_3$): δ (ppm)

7.09-7.07 (d, J=7.2 Hz, 1H), 7.06-7.04 (d, J=7.2 Hz, 2H), 6.93-6.89 (t, J=7.8 Hz, 1H), 6.93-6.89 (t, J=7.7 Hz, 2H), 6.58-6.56 (d, J=7.7 Hz, 2H), 6.56-6.54 (d, J=7.8 Hz, 2H), 6.35 (s, 1H), 5.87 (s, 1H), 3.84 (s, 6H), 3.83 (s, 3H).

Production Example 2 Production of 1,8,13-trimethoxytriptycene (Compound 5a) Single Crystal

[Chemical Formula 5]

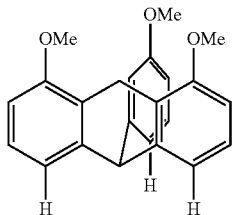

5a

The trimethoxytriptycene mixture (10.0 mg) produced in Production Example 1 was crystallized by dissolving in chloroform and allowing to stand, thereby obtaining 1,8,13-trimethoxytriptycene (2.0 mg) of the title.

The crystal thus obtained was subjected to the single-crystal X-ray structural analysis, and the result was as follows. This crystal had an orthorhombic crystal system, and the values of a, b, and c of unit cell were 15.608, 13.388, and 8.041, respectively in a unit of angstrom. The value of V was 1680 cubic angstrom.

Production Example 3 Production of 1,8,13-trihydroxytriptycene (Compound 6)

[Chemical Formula 6]

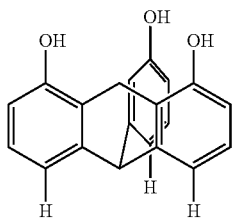

6

To the trimethoxytriptycene mixture (22.0 g, 62.9 mmol) produced in Production Example 1, 320 mL of dichloromethane was added to prepare a suspension, and boron tribromide ($BBr_3$) (18.2 mL, 192 mmol) was added to this, and the mixture was stirred for 4 hours at 0° C. To the reaction mixture, 200 mL of water was added, and the powder thus precipitated was collected by filtration and dried under reduced pressure. The powder thus obtained was dissolved in 80 mL of dimethylformamide, the mixture was allowed to stand at 5° C., and as a result, a colorless crystal was precipitated. This crystal was collected by filtration and washed with chloroform, thereby selectively obtaining 1,8,13-trihydroxytriptycene (Compound 6) (yield: 9.14 g, 71%) of the title.

Compound 6:
$^1$H-NMR (400 MHz, acetone-$d_6$): δ (ppm)
8.35 (br, s, 3H), 6.94-6.93 (d, J=7.2 Hz, 3H), 6.86 (s, 1H), 6.79-6.75 (dd, J=7.2, 0.9 Hz, 3H), 6.56-6.54 (dd, J=8.1, 0.9 Hz, 3H), 5.44 (s, 1H).

Production Example 4 Production of the Following Compound 1

[Chemical Formula 7]

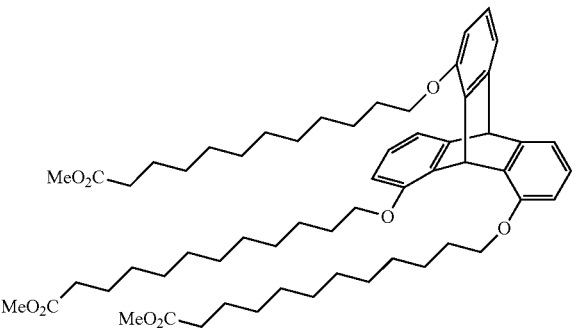

Compound 6 (102 mg, 0.337 mmol) produced in Production Example 3 was dissolved in 10.0 mL of dimethylformamide, potassium carbonate (190 mg, 1.34 mmol) and methyl 12-bromododecanoate (373 mg, 1.21 mmol) were added thereto, and the mixture was stirred for 10 hours at 70° C. To the reaction mixture, 50 mL of diethyl ether was added, the mixture was washed with water, and the organic layer was dried over magnesium sulfate, filtered, and distilled off under reduced pressure. The residue was subjected to the gel filtration chromatography using chloroform as a solvent, thereby obtaining Compound 1 (yield: 261 g, 82%) of the title.

Compound 1:
$^1$H-NMR (400 MHz, $CDCl_3$): δ (ppm)
6.99 (d, J=7.3 Hz, 3H), 6.89-6.84 (m, 4H), 6.54 (d, J=8.3 Hz, 3H), 5.37 (s, 1H), 3.96 (t, J=6.6 Hz, 6H), 3.67 (s, 9H), 1.85 (m, 6H), 1.705-1.270 (m, 60H),

Production Example 5 Production of the Following Compound 8

[Chemical Formula 8]

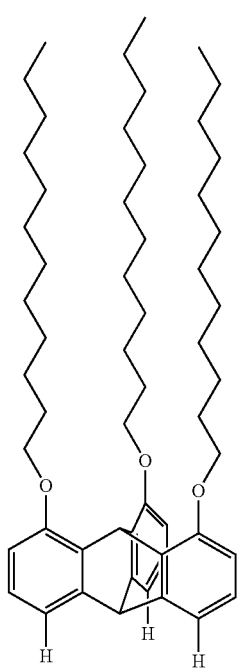

To Compound 6 (100 mg, 0.331 mmol) produced in Production Example 3 and potassium carbonate (274 mg, 1.98 mmol), 2.0 mL of dimethylformamide was added, the mixture was stirred, 1-bromododecane (990 mg, 3.97 mmol) was further added thereto, and the mixture was stirred for 8 hours at 75° C. while heating. The reaction mixture was cooled to room temperature, 300 mL of diethyl ether and water were added thereto, and the organic layer was separated. The organic layer was washed with saturated salt solution and water, the organic layer was then dried over magnesium sulfate, and the solvent was then distilled off under reduced pressure. The residue was subjected to the size exclusion chromatography using chloroform as a solvent, thereby obtaining Compound 8 (yield: 213 mg, 89%) of the title as white powder.

Compound 8:
$^1$H-NMR (400 MHz, acetone-$d_6$): δ (ppm)
7.99 (d, J=7.2 Hz, 3H), 7.91 (s, 1H), 7.89 (t, J=7.6 Hz, 3H), 7.55 (d, J=8.1 Hz, 3H), 3.95 (t, J=6.4 Hz, 6H), 1.85 (q, J=7.1 Hz, 6H), 1.60-1.55 (m, 6H), 1.36-1.28 (m, 54H), 0.89 (t, J=6.8 Hz, 9H).

Production Example 6 Production of the Following Compound 9

[Chemical Formula 9]

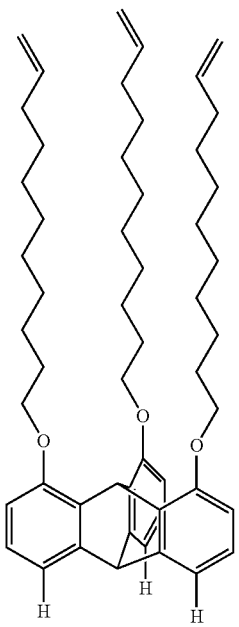

To Compound 6 (100 mg, 0.331 mmol) produced in Production Example 3 and potassium carbonate (365 mg, 2.64 mmol), 2.0 mL of dimethylformamide was added, the mixture was stirred, 11-bromododecene (608 mg, 2.61 mmol) was further added thereto, and the mixture was stirred for 12 hours at 80° C. while heating. The reaction mixture was cooled to room temperature, 200 mL of diethyl ether and water were added thereto, and the organic layer was separated. The organic layer was washed with water and saturated salt solution, the organic layer was then dried over magnesium sulfate, and the solvent was then distilled off under reduced pressure. The residue was subjected to the size exclusion chromatography using chloroform as a solvent, thereby obtaining Compound 9 (yield: 187 mg, 75%) of the title as white powder.

Compound 9:
$^1$H-NMR (400 MHz, acetone-$d_6$): δ (ppm)
6.99 (d, J=7.2 Hz, 3H), 6.89 (s, 1H), 6.87 (t, J=7.8 Hz, 3H), 6.54 (d, J=7.8 Hz, 3H), 5.37 (s, 1H), 3.96 (t, J=6.4 Hz, 6H), 2.19 (td, J=7.1 Hz, J=2.6 Hz, 6H), 1.94 (t, J=2.6 Hz, 3H), 1.85 (q, J=7.0 Hz, 6H), 1.58-1.50 (m, 12H), 1.41-1.35 (m, 24H).

Production Example 7 Production of the Following Compound 10

[Chemical Formula 10]

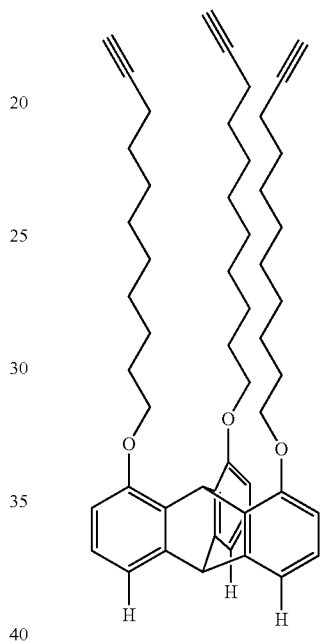

To Compound 6 (160 mg, 0.221 mmol) produced in Production Example 3 and potassium carbonate (365 mg, 2.64 mmol), 2.0 mL of dimethylformamide was added, the mixture was stirred, 11-bromododecyne (608 mg, 2.61 mmol) was further added thereto, and the mixture was stirred for 12 hours at 80° C. while heating. The reaction mixture was cooled to room temperature, 200 mL of diethyl ether and water were added thereto, and the organic layer was separated. The organic layer was washed with water and saturated salt solution, the organic layer was then dried over magnesium sulfate, and the solvent was then distilled off under reduced pressure. The residue was subjected to the size exclusion chromatography using chloroform as a solvent, thereby obtaining Compound 10 (yield: 99.3 mg, 47%) of the title as white powder.

Compound 10:
$^1$H-NMR (300 MHz, acetone-$d_6$): δ (ppm)
7.00 (d, J=7.2 Hz, 3H), 6.90 (s, 1H), 6.87 (t, J=7.8 Hz, 3H), 6.55 (d, J=7.5 Hz, 3H), 5.87-5.75 (m, 3H), 5.04-4.92 (m, 6H), 5.37 (s, 1H), 3.96 (d, J=6.6 Hz, 6H), 2.08-2.01 (m, 6H), 1.85 (q, J=6.6 Hz, 6H), 1.65-1.51 (m, 12H), 1.36-1.32 (m, 24H).

Production Example 8 Production of the Following Compound 11

[Chemical Formula 11]

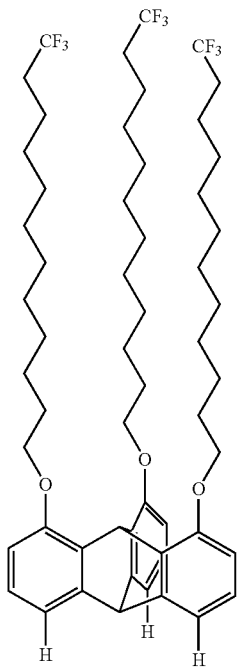

To Compound 9 (160 mg, 0.221 mmol) produced in Production Example 6, a trifluoromethylating agent (J. Am. Chem. Soc., 2011, 133, 16410) (316 mg, 1.00 mmol) represented by the following Formula:

[Chemical Formula 12]

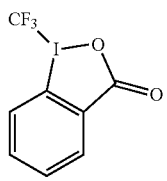

and copper(I) chloride (9.90 mg, 0.100 mmol), 2.0 mL of dimethyl formamide was added, and the mixture was frozen to degas and stirred for 30 minutes at 70° C. while heating under argon. To the reaction mixture, 300 mL of water was added, and the solid thus precipitated was separated by filtration and subjected to the silica gel chromatography using a mixed solvent of hexane-dichloromethane (2:1, v/v) as a developing solvent. To the white powder (119 mg) thus obtained, 5% palladium carbon (24 mg), 50 mL of tetrahydrofuran, and 50 mL of ethanol were added, and the mixture was stirred for 12 hours at room temperature under a hydrogen gas atmosphere. The reaction mixture was filtered through a pad of celite, and the solvent was distilled off under reduced pressure. The residue was subjected to the silica gel chromatography using a mixed solvent of hexane-dichloromethane (2:1, v/v) as a developing solvent, thereby obtaining Compound 11 (yield: 196 mg, 78%) of the title as white powder.

Compound 11:
$^1$H-NMR (400 MHz, CDCl$_3$): δ (ppm)
7.00 (d, 3H, J=7.4 Hz), 6.89 (s, 1H), 6.87 (dd, 3H, J=7.4, 7.4 Hz), 6.55 (d, 3H, J=7.4 Hz), 5.37 (s, 1H), 3.96 (t, 6H, J=6.5 Hz), 1.85 (m, 6H), 1.61-1.51 (tt, 6H, J=6.5, 6.5 Hz), 1.43-1.29 (m, 36H).

Production Example 9 Identification of Assembled Structure of Compound 1

The powder of Compound 1 was annealed at 240° C. and cooled to 25° C. to produce an assembled structure of Compound 1.

The assembled structure of Compound 1 thus produced has been demonstrated to form a lamellar integrated structure consisting of a layer having the benzene rings with a three-blade shape packed in a nesting shape and a layer of a long-chain alkyl group by the powder X-ray diffraction measurement. The interlayer distance of about 2.4 nm was observed by the powder X-ray diffraction measurement, and this is consistent with the length of the longitudinal direction of Compound 1. The above result indicates that functional groups or groups having functions can be highly densely integrated in a layer shape by utilizing the assembling behavior of the present Janus-type molecule.

Production Example 10

The formation of a film was conducted at a liquid/liquid interface formed by water and an organic solvent using the present Janus-type triptycene (Compound 1). It was possible to form a film on a scale of a few cm$^2$, and a flexible film was obtained. The film was transferred to a glass substrate and subjected to the X-ray diffraction measurement. The result has demonstrated that the layer structure is formed parallel to the substrate. In addition, the film thickness is about from 50 to several hundreds nm, and the thinnest portion of the film is considered to correspond to a layer of about 20 molecules.

Furthermore, the degree of thinning and high strengthening of film-shaped structure was measured.

Production Example 11 Production of Film on Glass Substrate Using Compound 1

On a mica substrate, 50 μL of a THF solution of Compound 1 (1 mg/200 mL, about 5.3 μM) was drop-casted.

This was naturally dried, and the film thus produced was subjected to a measurement by an atomic force microscope (AFM).

The result of AFM measurement is illustrated in FIG. 3.

Production Example 12 Production of Film on Mica Substrate Using Compound 1

On a mica substrate, 50 μL of a THF solution of Compound 1 (1 mg/200 mL, about 5.3 μM) was drop-casted.

This was naturally dried, and the film thus produced was subjected to a measurement by an atomic force microscope (AFM).

The result of AFM measurement is illustrated in FIG. 4.

Production Example 13 Production of Film on Mica Substrate Using Compound 1

On a glass substrate, 50 μL of a THF solution of Compound 1 (1 mg/200 mL, about 5.3 WO was drop-casted.

This was naturally dried.

Subsequently, this was annealed for 20 minutes at 180° C. in the air.

The film thus produced was subjected to a measurement by an atomic force microscope (AFM).

The result of AFM measurement is illustrated in FIG. 5.

Production Example 14 Production of Film Using Compound 8 by Vapor Deposition Method The substrate temperature of a silicon substrate was set to 25° C. and Compound 8 produced in Production Example 5 was heated to about 200° C. that is higher than the melting point thereof to conduct vacuum deposition using a usual vacuum deposition apparatus under a reduced pressure environment of $4 \times 10^{-4}$ Pa. The film thickness of the vapor deposited film thus obtained was 62 nm.

The molecular orientation in the film thus obtained was measured by the grazing incidence X-ray diffraction method (GIXD), and as a result, it has been revealed that the film is a regularly orientated molecular film having an interval of $d_{110}$ of 0.41 nm. It has been revealed that the interval of the triptycene skeletal structure in the orientated molecular film is 0.81 nm from this result as well.

A flat (monodomain) film having a film thickness of 2.5 nm was obtained by annealing the film formed on a silicon substrate by the method described above for 60 minutes at 120° C.

Production Example 15

Compound 8 produced in Production Example 5 was vacuum deposited on a quartz substrate, a mica substrate, a polyimide substrate, and a PET substrate, respectively, by the same method as in Production Example 14. The thickness of each of the films thus obtained was 50 nm.

The molecular orientation in each of the films thus obtained was measured by GIXD in the same manner as in Production Example 14, and as a result, it has been revealed that each of the films is a regularly orientated molecular film having an interval of $d_{110}$ of about 0.41 nm.

Production Example 16

On a sapphire substrate, Compound 8 produced in Production Example 5, Compound 9 produced in Production Example 6, Compound 10 produced in Production Example 7, and Compound 11 produced in Production Example 8 were vacuum deposited, respectively, by the same method as in Production Example 14. The film thickness of the films thus obtained was 50 nm, respectively.

The vapor deposited film produced using Compound 10 was subjected to a measurement by the attenuated total reflection infrared absorption spectrum (ATR-IR), and it was possible to confirm the characteristic absorption of a carbon-carbon triple bond.

Production Example 17

Production of Film on Silicon Substrate Using Compound 8 Produced in Production Example 5

A toluene solution of Compound 8 (200 μM, 50 μL) was spin-coated on a silicon substrate at 2300 rpm. A monolayer was formed by setting the coating amount to an amount to be enough for the formation of a monolayer.

This was naturally dried, the film thus produced was subjected to a measurement by an atomic force microscope (AFM), and as a result, the film thickness was about 1.9 nm.

It was possible to obtain an extremely flat film as this was annealed for 1 hour at 150° C. The same result was obtained even when the annealing was conducted for 1 hour at 80° C. by toluene vapor.

Example 1

A transistor 10 was manufactured using a film produced using Compound 1.

The schematic view of the transistor 10 is illustrated in FIG. 6.

Aluminum was deposited on a silicon wafer and patterned, and subsequently incinerated in an oxygen plasma to have a surface of aluminum oxide, and then an $Al_2O_3/Al$ gate electrode 11 and a gate insulating layer 12 compound of aluminum oxide were patterned. On this, 10 μL of a solution of Compound 1 (2 mg/50 mL) was drop-casted and dried. Thereafter, the resultant was annealed for 20 minutes at about 200° C. to obtain an organic thin film 13 having a film thickness of about 2.6 nm. An organic semiconductor composed of DNTT (dinaphthothienothiophene) was vacuum deposited on the organic thin film 13 formed on the $Al_2O_3/Al$ gate electrode 11 thus patterned to form an organic semiconductor layer 14. Thereafter, gold was deposited on the organic semiconductor layer 14 by the vacuum deposition method to form a source electrode 16 and a drain electrode 15. The pattern formation of the source electrode 16 and drain electrode 15 was conducted using a shadow mask at the time of the vacuum deposition.

The capacitance of the transistor 10 thus obtained was 644 nF/cm², the electron mobility was 0.387 cm²/Vs, the on-off ratio was $7.32 \times 10^6$, the threshold voltage was −0.487 V, and the leakage current was $9.44 \times 10^{-11}$ A.

Comparative Example 1

The same transistor was manufactured by forming the organic semiconductor layer directly on the aluminum oxide without performing the formation of the organic thin film using Compound 1 in Example 1.

The capacitance of the transistor thus obtained was 710 nF/cm², the electron mobility was 0.504 cm²/Vs, the on-off ratio was $5.14 \times 10^5$, the threshold voltage was −0.709 V, and the leakage current was $2.86 \times 10^{-10}$ A.

Example 2

A transistor 20 is manufactured using the Janus-type triptycene derivative represented by Formula [I] of the present invention.

As the gate insulating layer, Parylene (registered trademark) is used to form a gate insulating layer 22, and gold is used as a gate electrode 21. Thereafter, in the same manner as in Example 1, an organic thin film 23 by the Janus-type triptycene derivative of the present invention is formed on the gate insulating layer 22, an organic semiconductor layer 24 is formed thereon, and a drain electrode 25 and a source electrode 26 of gold are further formed thereon.

In a case in which $R^2$ in Formula [I] is an aryl group or a heteroaryl group such as a phenyl group as the Janus-type triptycene derivative represented by Formula [I], this moiety functions as an organic semiconductor, and thus it is also possible to omit the organic semiconductor layer 24.

Example 3

A transistor 30 illustrate in FIG. 7 was manufactured using the following compound 7 as a material compound of the organic thin film.

[Chemical Formula 13]

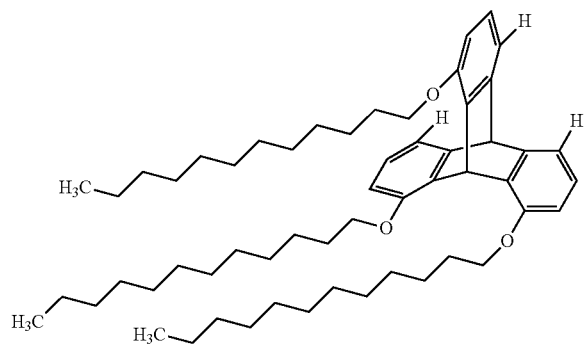

Patterned gold was deposited on a polyimide (PI) film as a gate electrode 31. Parylene (registered trademark, paraxylylene-based resin) was deposited by CDV so as to cover the gate electrode 31 thus patterned and annealed for 1.5 hours at 120° under a nitrogen stream, thereby forming a first gate insulating layer 32. On the first gate insulating layer 32 composed of each Parylene (registered trademark) described above, 10 µL of a mesitylene solution of Compound 7 described above (solution prepared by dissolving 5.0 mg of Compound 7 in 50 mL of mesitylene) was casted and annealed for 1.5 hours at 100° C. under a nitrogen stream, whereby an organic thin film 33 of Compound 7 serving as a second gate insulating film was formed so as to cover the first gate insulating layer 32. An organic semiconductor composed of DNTT (dinaphthothienothiophene) was vacuum deposited on the organic thin film 33 in order to obtain a p-type semiconductor, thereby forming an organic semiconductor layer 34. Subsequently, a gold electrode was deposited on the organic semiconductor layer 34 to obtain a drain electrode 35 and a source electrode 36.

In Compound 7, the end of the alkyl chain is a methyl group ($CH_3$—) but not a functional group such as a mercapto group (HS—). Hence, the Janus-type triptycene derivative represented by Formula [I] of the present invention can form a high-quality organic thin film without being dependent on the nature of material for the surface. In particular, the fact that it is possible to form a highly flat organic thin film layer which is densely arranged on Parylene (registered trademark) of an organic material makes it possible to form a gate insulating layer without film-forming defects on a flexible plastic substrate such as polyimide or polyethylene terephthalate at a low temperature. The use of the organic thin film 33 composed of Compound 7 makes it possible to modify and control the interface between the gate insulating layer and an organic semiconductor layer at which the current of the thin film transistor concentrates, and thus it is possible to realize a high-performance flexible organic thin film transistor array.

The capacitance of the transistor 30 thus obtained was 43.1 $nF/cm^2$, the electron mobility was 1.9 $cm^2/Vs$, the on-off ratio was $4.4×10^7$, the threshold voltage was −0.52 V, and the maximum leakage current was −32 pA.

Comparative Example 2

A transistor without an organic thin film was manufactured by forming the organic semiconductor layer 34 directly on the gate insulating layer 32 without performing the formation of the organic thin film using Compound 7 in Example 3.

The capacitance of the transistor thus obtained was 42.6 $nF/cm^2$, the electron mobility was 0.60 $cm^2/Vs$, the on-off ratio was about $10^7$, and the threshold voltage was −0.8 V.

As described above, the organic thin film transistor using the organic two-layered gate insulating film having modified interface of the present Example resulted in an extremely high improvement in mobility. In addition, it was possible to realize a high on-off ratio by the effect of the organic gate insulating film at the same time.

Example 4

As an organic thin film, a 4,5,16-triphenyl form of Compound 7 was used. The phenyl group moiety 433 of the 4,5,16-triphenyl form of Compound 7 used in the present Example also functions as an organic semiconductor, and thus the formation of an organic semiconductor layer composed of DNTT in Example 3 was omitted. Except this, a transistor 40 illustrated in FIG. 8 was manufactured in the same manner as in Example 3.

In the same manner as in Example 3, a gate electrode 41 of gold was formed on a polyimide (PI) film, a first gate insulating layer 42 composed of Parylene (registered trademark, paraxylylene-based resin) was formed so as to cover it. Thereafter, an organic thin film 43 serving as a second gate insulating film was formed using the 4,5,16-triphenyl form of the Janus-type triptycene derivative, and a gold electrode was deposited thereon to use as a drain electrode 45 and a source electrode 46. The organic thin film 43 of the transistor 40 is composed of an alkyl chain moiety 431, a triptycene skeletal structure moiety 432, and a phenyl group moiety 433. The phenyl group moiety 433 itself also functions as an organic semiconductor.

In this configuration, the boundary of the gate insulating layer and the semiconductor layer of a transistor is included in the interior of the organic thin film 43 consisting of a single layer of the Janus-type triptycene derivative. In the related art, the gate insulating layer and the semiconductor layer are formed in a layered body composed of different materials and thus the interface thereof has a structure that is greatly affected by the continuous film forming processes, but in the present Example, the interface that is greatly related to the performance and quality of a thin film organic transistor is formed in the interior of a single chemical substance and thus it is possible to fabricate a transistor exhibiting high performance and stable quality without being dependent on the film forming process.

Example 5

In Example 4, the transistors 40 without an organic semiconductor layer was manufactured since the plane of the phenyl group of the 4,5,16-triphenyl form of Compound 7 which was used functions as an organic semiconductor, but it is also possible to further provide an organic semiconductor layer composed of DNTT or the like. A transistor 50 further provided with an organic semiconductor layer 54 to the transistor 40 which was manufactured in Example 4 is manufactured.

FIG. 9 illustrates only the portions of the organic thin film 53 composed of the 4,5,16-triphenyl form of Compound 7 and the organic semiconductor layer 54. The organic thin film 53 is composed of an alkyl chain moiety 531, a triptycene skeletal structure moiety 532, and a phenyl group moiety 533, and the organic semiconductor layer 54 is formed on the phenyl group moiety 533.

In this configuration, although there is an interface between the organic thin film 53 and the organic semiconductor layer 54, the interface can be an interface excellent in affinity since both of them are organic-based materials.

Example 6

In Example 3, Compound 7 was used as the organic thin film of the present invention, but a transistor 60 is manufactured in the same manner as in Example 4 using the 4,5,16-triphenyl form of the Janus-type triptycene derivative represented by Formula [I] instead of Compound 7.

In addition, it is also possible to further provide an organic semiconductor layer 64 as described in Example 5.

Example 7

A transistor 70 illustrated in FIG. 10 is manufactured.

The transistor 70 is manufactured using the 4,5,16-triphenyl form of the Janus-type triptycene derivative represented by Formula [I] of the present invention as an organic thin film and including a gate insulating layer 72, an organic thin film 73 of the present invention, electrodes 75 and 76, and an organic semiconductor layer 74 in this order so that the source electrode 76 and the drain electrode 75 were positioned on the lower side of the organic semiconductor layer 74.

The organic thin film 73 of the present invention in FIG. 10 is composed of an alkyl chain moiety 731, a triptycene skeletal structure moiety 732, and a phenyl group moiety 733, and the phenyl group moiety 733 of the organic thin film not only has affinity for the organic semiconductor layer but also functions as an organic semiconductor itself in the same manner as in Example 6.

In addition, it is also possible to use a 4,5,16-unsubstituted form (namely, a compound in which $R^2$ of Formula [I] is a hydrogen atom) instead of the 4,5,16-triphenyl form.

Incidentally, the —$R^1$—Z moiety of Formula [I] is illustrated as an alkyl chain in FIG. 10 for convenience.

Example 8

A transistor 80 illustrated in FIG. 11 is manufactured.

A gate insulating layer 82 composed of Parylene (registered trademark) is formed on a gate electrode 81. A source electrode 86 and a drain electrode 85 are formed on the gate insulating layer 82 composed of Parylene (registered trademark). An organic thin film 83 of the present invention is formed thereon in the direction in which the triptycene skeletal structure moiety of the Janus-type triptycene derivative of the present invention is in contact with the source electrode and the drain electrode. The top of the organic thin film thus formed is covered with a sealing layer 87, thereby manufacturing the transistor 80.

The triptycene skeletal structure moiety of the organic thin film functions as an organic semiconductor.

In addition, it is also possible to use a compound in which the positions of 4, 5, and 16 are substituted with various kinds of aryl groups such as a phenyl group or heteroaryl groups, for example, polythiophene, polyphenyl or the like instead of the compound used as the organic thin film in the present Example.

Incidentally, the —$R^1$—Z moiety of Formula [I] is illustrated as an alkyl chain in FIG. 11 for convenience.

INDUSTRIAL APPLICABILITY

The present invention provides a novel organic thin film that can form an extremely homogeneous and clean interface between an organic semiconductor layer and an insulator layer. The use of the organic thin film of the present invention makes it possible to achieve an improvement in performance, homogeneity, and stability of an electronic device, in particular, an organic thin film transistor. Furthermore, it is possible to form a uniform electronic device, in particular, a transistor over a large area upon realizing a large-area flexible electronic device. The present invention is intended to provide an electronic device and various kinds of electronic apparatuses using the electronic device, and has industrial applicability in the electronic field and the like.

REFERENCE SIGNS LIST

10, 30, 40, 50, 70, and 80 Transistor of the present invention
11, 31, 41, 71, and 81 Gate electrode
12, 32, 42, 72, and 82 Gate insulating layer
13, 33, 43, 53, 73, and 83 Organic thin film of the present invention
14, 34, 54, and 74 Organic semiconductor layer
15, 35, 45, 75, and 85 Drain electrode
16, 36, 46, 76, and 86 Source electrode
87 Sealing layer
90, 100 Capacitor of the present invention
91, 101 Substrate
92, 102 Electrode
93, 103 Organic thin film of the present invention (first dielectric)
104 Second dielectric

The invention claimed is:
1. An electronic device comprising, as a component:
an organic thin film comprising a Janus-type triptycene derivative represented by the following Formula [I];

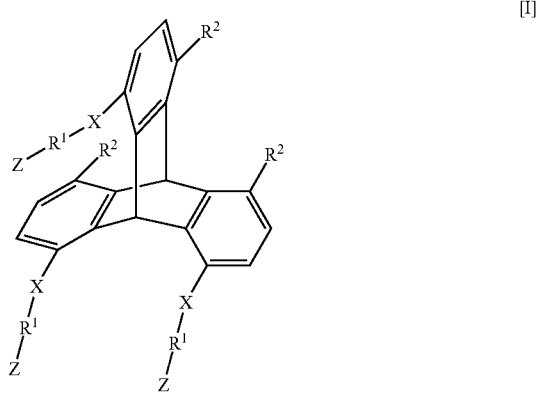

(in Formula [I], three $R^1$'s are an identical group, $R^1$ represents a divalent saturated or unsaturated hydrocarbon group having from 2 to 60 carbon atoms, the hydrocarbon group may optionally have one or more substituents, and one or more carbon atoms in the hydrocarbon group may be optionally substituted with oxygen atom, sulfur atom, silicon atom, or —NR$^5$— (here, R$^5$ represents a hydrogen atom, an alkyl group having from 1 to 10 carbon atoms, or an aryl group having from 6 to 30 carbon atoms), three R$^2$'s are the same as or different from one another and each independently represent a group different from a group —X—R$^1$—Z, and R$^2$ represents a hydrogen atom, a halogen atom, a hydroxyl group, a nitro group, a cyano group, an amino group, a mono alkyl-substituted amino group, a dialkyl-substituted amino group, an alkyl group which has from 1 to 10 carbon atoms and may optionally have one or more substituents, an alkenyl group which has from 2 to 10 carbon atoms and may optionally have one or more substituents, an alkynyl group which has from 2 to 10 carbon atoms and may optionally have one or more substituents, an alkoxy group which has from 1 to 10 carbon atoms and may optionally have one or more substituents, an alkylthio group which has from 1 to 10 carbon atoms and may optionally have one or more substituents, a formyl group, an alkylcarbonyl group which has from 1 to 10 carbon atoms and may optionally have one or more substituents, an alkoxycarbonyl group which has from 1 to 10 carbon atoms and may optionally have one or more substituents, an alkylcarbonyloxy group which has from 1 to 10 carbon atoms and may optionally have one or more substituents, an aryl group which has from 6 to 30 carbon atoms and may optionally have one or more substituents, or a 5- to 8-membered heteroaryl group which has from 1 to 5 heteroatoms selected from the group consisting of nitrogen atom, oxygen atom, and sulfur atom and from 2 to 10 carbon atoms and may optionally have one or more substituents, three X's are an identical group, and X represents a linker group consisting of a divalent atomic group composed of from 1 to 5 atoms selected from the group consisting of nitrogen atom, oxygen atom, sulfur atom, carbon atom, and silicon atom, and one or more hydrogen atoms if necessary, and three Z's are an identical group, and Z represents a hydrogen atom, a group capable of being bonded to or adsorbed on a surface of a solid substrate, or an end group consisting of a monovalent atomic group composed of from 1 to 15 atoms selected from the group consisting of nitrogen atom, oxygen atom, sulfur atom, carbon atom, phosphorus atom, halogen atom, and silicon atom, and one or more hydrogen atoms if necessary).

2. The electronic device according to claim 1, wherein the electronic device is a transistor, a capacitor, a diode, a thyristor, an electroluminescent device, a sensor, or a memory.

3. The electronic device according to claim 2, wherein the electronic device is a capacitor.

4. The electronic device according to claim 3, wherein the capacitor is a capacitor having a dielectric layer comprising a first dielectric composed of the organic thin film between electrodes.

5. The electronic device according to claim 4, wherein the dielectric layer further comprises a second dielectric.

6. The electronic device according to claim 5, wherein the second dielectric is an organic dielectric.

7. The electronic device according to claim 5, wherein the organic thin film and the second dielectric are in a layered structure.

8. The electronic device according to claim 1, wherein the electronic device is a thin film transistor.

9. The electronic device according to claim 8, wherein the thin film transistor is an organic thin film transistor including a gate electrode, a source electrode, a drain electrode, and a gate insulating layer on a substrate.

10. The electronic device according to claim 9, wherein the gate insulating layer comprises an insulating material and the organic thin film.

11. The electronic device according to claim 10, wherein the gate insulating layer comprises a layered body of the insulating material and the organic thin film.

12. The electronic device according to claim 10, wherein the insulating material of the gate insulating layer is an organic insulating material.

13. The electronic device according to claim 9, wherein the thin film transistor further includes a channel layer composed of a semiconductor.

14. The electronic device according to claim 13, wherein the channel layer is an organic semiconductor layer.

15. The electronic device according to claim 14, wherein a boundary portion between the gate insulating layer and the organic semiconductor layer in the thin film transistor includes the organic thin film.

16. The electronic device according to claim 15, wherein the gate insulating layer, the organic thin film and the organic semiconductor layer are in a layered structure.

17. The electronic device according to claim 15, wherein the three groups —X—R$^1$—Z are oriented on the gate insulating layer side and the three R$^2$'s are oriented on the organic semiconductor layer side.

18. The electronic device according to claim 13, wherein the organic thin film and the semiconductor of the channel layer are layered.

19. The electronic device according to claim 13, wherein the source electrode and/or the drain electrode of the thin film transistor is formed between the organic thin film and the channel layer.

20. The electronic device according to claim 19, wherein the channel layer is an organic semiconductor layer.

21. A circuit board comprising:
the electronic device according to claim 1 in an electronic circuit.

22. An electronic apparatus comprising:
the electronic device according to claim 1 in the interior thereof.

23. The electronic apparatus according to claim 22, being an electronic paper, an organic EL display, or a liquid crystal display.

24. An electronic device material comprising an organic thin film comprising a Janus-type triptycene derivative represented by the following Formula [I];

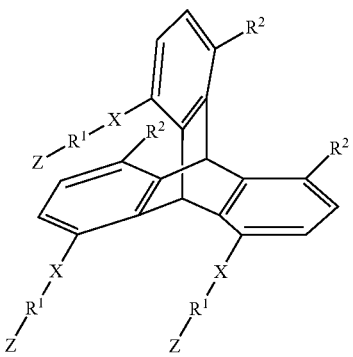

[I]

(in Formula [I], three $R^1$'s are an identical group, $R^1$ represents a divalent saturated or unsaturated hydrocarbon group having from 2 to 60 carbon atoms, the hydrocarbon group may optionally have one or more substituents, and one or more carbon atoms in the hydrocarbon group may be optionally substituted with oxygen atom, sulfur atom, silicon atom, or —$NR^5$— (here, $R^5$ represents a hydrogen atom, an alkyl group having from 1 to 10 carbon atoms, or an aryl group having from 6 to 30 carbon atoms), three $R^2$'s are the same as or different from one another and each independently represent a group different from a group —X—$R^1$—Z, and $R^2$ represents a hydrogen atom, a halogen atom, a hydroxyl group, a nitro group, a cyano group, an amino group, a mono alkyl-substituted amino group, a dialkyl-substituted amino group, an alkyl group which has from 1 to 10 carbon atoms and may optionally have one or more substituents, an alkenyl group which has from 2 to 10 carbon atoms and may optionally have one or more substituents, an alkynyl group which has from 2 to 10 carbon atoms and may optionally have one or more substituents, an alkoxy group which has from 1 to 10 carbon atoms and may optionally have one or more substituents, an alkylthio group which has from 1 to 10 carbon atoms and may optionally have one or more substituents, a formyl group, an alkylcarbonyl group which has from 1 to 10 carbon atoms and may optionally have one or more substituents, an alkoxycarbonyl group which has from 1 to 10 carbon atoms and may optionally have one or more substituents, an alkylcarbonyloxy group which has from 1 to 10 carbon atoms and may optionally have one or more substituents, an aryl group which has from 6 to 30 carbon atoms and may optionally have one or more substituents, or a 5- to 8-membered heteroaryl group which has from 1 to 5 heteroatoms selected from the group consisting of nitrogen atom, oxygen atom, and sulfur atom and from 2 to 10 carbon atoms and may optionally have one or more substituents, three X's are an identical group, and X represents a linker group consisting of a divalent atomic group composed of from 1 to 5 atoms selected from the group consisting of nitrogen atom, oxygen atom, sulfur atom, carbon atom, and silicon atom, and one or more hydrogen atoms if necessary, and three Z's are an identical group, and Z represents a hydrogen atom, a group capable of being bonded to or adsorbed on a surface of a solid substrate, or an end group consisting of a monovalent atomic group composed of from 1 to 15 atoms selected from the group consisting of nitrogen atom, oxygen atom, sulfur atom, carbon atom, phosphorus atom, halogen atom, and silicon atom, and one or more hydrogen atoms if necessary).

* * * * *